(12) United States Patent
Melnyk et al.

(10) Patent No.: US 9,029,503 B2
(45) Date of Patent: May 12, 2015

(54) METHOD FOR NATIVE LIGATION OF POLYPEPTIDES

(75) Inventors: Oleg Melnyk, Annoeullin (FR); Reda Mhidia, Mons en Baroeul (FR); Julien Dheur, La Bassee (FR); Nathalie Ollivier, Roubaix (FR)

(73) Assignees: Centre National de la Recherche Scientifique, Paris (FR); Institut Pasteur de Lille, Lille Cedex (FR)

( * ) Notice: Subject to any disclaimer, the term of this patent is extended or adjusted under 35 U.S.C. 154(b) by 231 days.

(21) Appl. No.: 13/504,054

(22) PCT Filed: Oct. 28, 2010

(86) PCT No.: PCT/IB2010/054897
§ 371 (c)(1),
(2), (4) Date: Apr. 25, 2012

(87) PCT Pub. No.: WO2011/051906
PCT Pub. Date: May 5, 2011

(65) Prior Publication Data
US 2012/0220721 A1      Aug. 30, 2012

(30) Foreign Application Priority Data

Oct. 29, 2009 (FR) ...................................... 09 57639

(51) Int. Cl.
*C07K 1/10* (2006.01)
*C07K 2/00* (2006.01)
*C07K 1/02* (2006.01)

(52) U.S. Cl.
CPC ..................................... *C07K 1/026* (2013.01)

(58) Field of Classification Search
CPC ............ C07K 1/026; C07K 1/02; C07K 1/00; C07K 1/061; C07K 1/10; C07K 2/00; C07K 17/08; C07K 17/02; C07K 17/00
USPC ...................................................... 530/330
See application file for complete search history.

(56) References Cited

FOREIGN PATENT DOCUMENTS

| CN | 1200147 A | 11/1998 |
|---|---|---|
| WO | WO 96/34878 A1 | 11/1996 |
| WO | WO-97/09428 | 3/1997 |
| WO | WO 98/28434 A1 | 7/1998 |
| WO | WO 01/68565 A2 | 9/2001 |
| WO | WO 01/87920 A2 | 11/2001 |
| WO | WO 2007/037812 A1 | 4/2007 |

OTHER PUBLICATIONS

Oliveira et al., Bioconjugate Chem. (2003) 14, 144-152.*
Olliviera et al., (Organic Letters (2010) 12(22), 5238-5241.*
International Search Report from International Patent Application No. PCT/IB2010/054897, date Jan. 2, 2011.
Aufort, M. et al.; "Synthesis and biochemical evaluation of a cyclic RGD oxorhenium complex as a new lignad of alphaVbeta3 integrin"; European Journal of Medicinal Chemistry, Editions Scientifique Elsevier, Paris, France; vol. 44, No. 9, Sep. 1, 2009; pp. 3394-3401.
Quibell, M. et al.; "Synthesis of the 3-Repeat Region of Human Tau-2 by the Solid Phase Assembly of Backbone Amide-Protected Segments"; J. Am. Chem. Soc. 1995, 117, 11656-11668.
Harre, et al.; "An Efficient Method for Activation and Recycling of Trityl Resins"; Reactive & Functional Polymers; 1999 Elsevier Sciences, 41 (1999) 111-114.
Singh, S et al.; Efficient Asymmetric Synthesis of (S)- and (R)-*N*-Fmoc-S-Trityl-α-methylcysteine Using Camphorsultam as a Chriral Auxiliary; J. Org. Chem. 2004, 69, 4551-4554.

* cited by examiner

*Primary Examiner* — Karlheinz R Skowronek
*Assistant Examiner* — Catherine Mader
(74) *Attorney, Agent, or Firm* — Alston & Bird LLP

(57) ABSTRACT

The invention mainly relates to a method for manufacturing a polypeptide of formula:

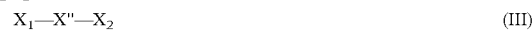

$X_1$—X"—$X_2$     (III)

$X_1$ and $X_2$ each representing a peptide fragment, and X" representing an amino acid residue comprising a thiol function, said method comprising at least one step of ligation reaction between a polypeptide of formula:

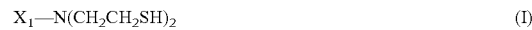

$X_1$—N(CH$_2$CH$_2$SH)$_2$     (I)

and a polypeptide of formula:

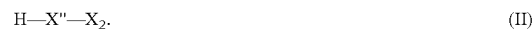

H—X"—$X_2$.     (II)

The invention also relates to the polypeptides of formula (I) themselves and the method for obtaining them, as well as resin supports suitable for obtaining them.

22 Claims, 4 Drawing Sheets

SEQUENCE LISTING

```
<160> NUMBER OF SEQ ID NOS: 23

<210> SEQ ID NO 1
<211> LENGTH: 8
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (8)..(8)
<223> OTHER INFORMATION: N(CH2CH2SH)2 group at the C-terminal end

<400> SEQUENCE: 1

Gly Phe Gly Gln Gly Phe Gly Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (9)..(9)
<223> OTHER INFORMATION: N(CH2CH2SH)2 group at the C-terminal end

<400> SEQUENCE: 2

Ile Leu Lys Glu Pro Val His Gly Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (9)..(9)
<223> OTHER INFORMATION: N(CH2CH2SH)2 group at the C-terminal end

<400> SEQUENCE: 3

Ile Leu Lys Glu Pro Val His Gly Ala
1               5

<210> SEQ ID NO 4
<211> LENGTH: 9
<212> TYPE: PRT
```

```
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (9)..(9)
<223> OTHER INFORMATION: N(CH2CH2SH)2 group at the C-terminal end

<400> SEQUENCE: 4

Ile Leu Lys Glu Pro Val His Gly Val
1               5

<210> SEQ ID NO 5
<211> LENGTH: 9
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (9)..(9)
<223> OTHER INFORMATION: N(CH2CH2SH)2 group at the C-terminal end

<400> SEQUENCE: 5

Ile Leu Lys Glu Pro Val His Gly Tyr
1               5

<210> SEQ ID NO 6
<211> LENGTH: 10
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (10)..(10)
<223> OTHER INFORMATION: NH2 group at the C-terminal end

<400> SEQUENCE: 6

Cys Ile Leu Lys Glu Pro Val His Gly Val
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (8)..(8)
<223> OTHER INFORMATION: N(CH2CH2SH)2 group at the C-terminal end

<400> SEQUENCE: 7

Cys His His Leu Glu Pro Gly Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Obtained by synthesis

<400> SEQUENCE: 8

Gly Phe Gly Gln Gly Phe Gly Gly
1               5

<210> SEQ ID NO 9
```

```
<211> LENGTH: 19
<212> TYPE: PRT
<213> ORGANISM: Artificial Sequence
<220> FEATURE:
<223> OTHER INFORMATION: Obtained by ligation
<220> FEATURE:
<221> NAME/KEY: MISC_FEATURE
<222> LOCATION: (19)..(19)
<223> OTHER INFORMATION: NH2 group at the C-terminal end

<400> SEQUENCE: 9

Ile Leu Lys Glu Pro Val His Gly Gly Cys Ile Leu Lys Glu Pro Val
1               5                   10                  15

His Gly Val

<210> SEQ ID NO 10
<211> LENGTH: 19
<212> TYPE: PRT
<213> ORGANISM: Artificial Sequence
<220> FEATURE:
<223> OTHER INFORMATION: Obtained by ligation
<220> FEATURE:
<221> NAME/KEY: MISC_FEATURE
<222> LOCATION: (19)..(19)
<223> OTHER INFORMATION: NH2 group at the C-terminal end

<400> SEQUENCE: 10

Ile Leu Lys Glu Pro Val His Gly Ala Cys Ile Leu Lys Glu Pro Val
1               5                   10                  15

His Gly Val

<210> SEQ ID NO 11
<211> LENGTH: 19
<212> TYPE: PRT
<213> ORGANISM: Artificial Sequence
<220> FEATURE:
<223> OTHER INFORMATION: Obtained by ligation
<220> FEATURE:
<221> NAME/KEY: MISC_FEATURE
<222> LOCATION: (19)..(19)
<223> OTHER INFORMATION: NH2 group at the C-terminal end

<400> SEQUENCE: 11

Ile Leu Lys Glu Pro Val His Gly Tyr Cys Ile Leu Lys Glu Pro Val
1               5                   10                  15

His Gly Val

<210> SEQ ID NO 12
<211> LENGTH: 8
<212> TYPE: PRT
<213> ORGANISM: Artificial Sequence
<220> FEATURE:
<223> OTHER INFORMATION: Obtained by ligation
<220> FEATURE:
<221> NAME/KEY: MISC_FEATURE
<222> LOCATION: (1)..(8)
<223> OTHER INFORMATION: Cyclic peptide

<400> SEQUENCE: 12

Cys His His Leu Glu Pro Gly Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Obtained by synthesis
```

```
<220> FEATURE:
<221> NAME/KEY: MISC_FEATURE
<222> LOCATION: (9)..(9)
<223> OTHER INFORMATION: Dithiazepane group at the C-terminal end

<400> SEQUENCE: 13

Ile Leu Lys Glu Pro Val His Gly Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (9)..(9)
<223> OTHER INFORMATION: Dithiazepane group at the C-terminal end

<400> SEQUENCE: 14

Ile Leu Lys Glu Pro Val His Gly Ala
1               5

<210> SEQ ID NO 15
<211> LENGTH: 9
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (9)..(9)
<223> OTHER INFORMATION: Dithiazepane group at the C-terminal end

<400> SEQUENCE: 15

Ile Leu Lys Glu Pro Val His Gly Val
1               5

<210> SEQ ID NO 16
<211> LENGTH: 9
<212> TYPE: PRT
<213> ORGANISM: Artificial Sequence
<220> FEATURE:
<223> OTHER INFORMATION: Obtained by synthesis
<220> FEATURE:
<221> NAME/KEY: MISC_FEATURE
<222> LOCATION: (9)..(9)
<223> OTHER INFORMATION: Dithiazepane group at the C-terminal end

<400> SEQUENCE: 16

Ile Leu Lys Glu Pro Val His Gly Tyr
1               5

<210> SEQ ID NO 17
<211> LENGTH: 10
<212> TYPE: PRT
<213> ORGANISM: Artificial Sequence
<220> FEATURE:
<223> OTHER INFORMATION: Obtained by synthesis or ligation
<220> FEATURE:
<221> NAME/KEY: MISC_FEATURE
<222> LOCATION: (1)..(1)
<223> OTHER INFORMATION: Homocysteine
<220> FEATURE:
<221> NAME/KEY: MISC_FEATURE
<222> LOCATION: (10)..(10)
<223> OTHER INFORMATION: NH2 group at the C-terminal end

<400> SEQUENCE: 17
```

```
Xaa Ile Leu Lys Glu Pro Val His Gly Val
1               5                   10
```

<210> SEQ ID NO 18
<211> LENGTH: 19
<212> TYPE: PRT
<213> ORGANISM: Artificial Sequence
<220> FEATURE:
<223> OTHER INFORMATION: Obtained by synthesis or ligation
<220> FEATURE:
<221> NAME/KEY: MISC_FEATURE
<222> LOCATION: (10)..(10)
<223> OTHER INFORMATION: Homocysteine
<220> FEATURE:
<221> NAME/KEY: MISC_FEATURE
<222> LOCATION: (19)..(19)
<223> OTHER INFORMATION: NH2 group at the C-terminal end

<400> SEQUENCE: 18

```
Ile Leu Lys Glu Pro Val His Gly Gly Xaa Ile Leu Lys Glu Pro Val
1               5                   10                  15

His Gly Val
```

<210> SEQ ID NO 19
<211> LENGTH: 24
<212> TYPE: PRT
<213> ORGANISM: Artificial Sequence
<220> FEATURE:
<223> OTHER INFORMATION: Obtained by synthesis or ligation
<220> FEATURE:
<221> NAME/KEY: MISC_FEATURE
<222> LOCATION: (4)..(4)
<223> OTHER INFORMATION: Protection of the thiol group, -SH is replaced
      by -SSC(CH3)3
<220> FEATURE:
<221> NAME/KEY: MISC_FEATURE
<222> LOCATION: (24)..(24)
<223> OTHER INFORMATION: Dithiazepane group at the C-terminal end

<400> SEQUENCE: 19

```
Ile Arg Asn Cys Ile Ile Gly Lys Gly Arg Ser Tyr Lys Gly Thr Val
1               5                   10                  15

Ser Ile Thr Lys Ser Gly Ile Lys
            20
```

<210> SEQ ID NO 20
<211> LENGTH: 28
<212> TYPE: PRT
<213> ORGANISM: Artificial Sequence
<220> FEATURE:
<223> OTHER INFORMATION: Obtained by synthesis or ligation
<220> FEATURE:
<221> NAME/KEY: MISC_FEATURE
<222> LOCATION: (1)..(1)
<223> OTHER INFORMATION: Thiazolidine protection of the thiol group and
      the alpha amine group
<220> FEATURE:
<221> NAME/KEY: MISC_FEATURE
<222> LOCATION: (28)..(28)
<223> OTHER INFORMATION: Dithiazepane group at the C-terminal end

<400> SEQUENCE: 20

```
Cys Gln Pro Trp Ser Ser Met Ile Pro His Glu His Ser Phe Leu Pro
1               5                   10                  15

Ser Ser Tyr Arg Gly Lys Asp Leu Gln Glu Asn Tyr
            20                  25
```

<210> SEQ ID NO 21
<211> LENGTH: 33

```
<212> TYPE: PRT
<213> ORGANISM: Artificial Sequence
<220> FEATURE:
<223> OTHER INFORMATION: Obtained by synthesis or ligation
<220> FEATURE:
<221> NAME/KEY: MISC_FEATURE
<222> LOCATION: (33)..(33)
<223> OTHER INFORMATION: NH2 group at the C-terminal end

<400> SEQUENCE: 21

Cys Arg Asn Pro Arg Gly Glu Glu Gly Pro Trp Cys Phe Thr Ser
1               5                   10                  15

Asn Pro Glu Val Arg Tyr Glu Val Cys Asp Ile Pro Gln Cys Ser Glu
            20                  25                  30

Val

<210> SEQ ID NO 22
<211> LENGTH: 61
<212> TYPE: PRT
<213> ORGANISM: Artificial Sequence
<220> FEATURE:
<223> OTHER INFORMATION: Obtained by synthesis or ligation
<220> FEATURE:
<221> NAME/KEY: MISC_FEATURE
<222> LOCATION: (1)..(1)
<223> OTHER INFORMATION: Thiazolidine protection of the thiol group and
      the alpha amine group
<220> FEATURE:
<221> NAME/KEY: MISC_FEATURE
<222> LOCATION: (61)..(61)
<223> OTHER INFORMATION: NH2 group at the C-terminal end

<400> SEQUENCE: 22

Cys Gln Pro Trp Ser Ser Met Ile Pro His Glu His Ser Phe Leu Pro
1               5                   10                  15

Ser Ser Tyr Arg Gly Lys Asp Leu Gln Glu Asn Tyr Cys Arg Asn Pro
            20                  25                  30

Arg Gly Glu Glu Gly Gly Pro Trp Cys Phe Thr Ser Asn Pro Glu Val
        35                  40                  45

Arg Tyr Glu Val Cys Asp Ile Pro Gln Cys Ser Glu Val
    50                  55                  60

<210> SEQ ID NO 23
<211> LENGTH: 85
<212> TYPE: PRT
<213> ORGANISM: Artificial Sequence
<220> FEATURE:
<223> OTHER INFORMATION: Obtained by synthesis or ligation
<220> FEATURE:
<221> NAME/KEY: MISC_FEATURE
<222> LOCATION: (85)..(85)
<223> OTHER INFORMATION: NH2 group at the C-terminal end

<400> SEQUENCE: 23

Ile Arg Asn Cys Ile Ile Gly Lys Gly Arg Ser Tyr Lys Gly Thr Val
1               5                   10                  15

Ser Ile Thr Lys Ser Gly Ile Lys Cys Gln Pro Trp Ser Ser Met Ile
            20                  25                  30

Pro His Glu His Ser Phe Leu Pro Ser Ser Tyr Arg Gly Lys Asp Leu
        35                  40                  45

Gln Glu Asn Tyr Cys Arg Asn Pro Arg Gly Glu Glu Gly Gly Pro Trp
    50                  55                  60

Cys Phe Thr Ser Asn Pro Glu Val Arg Tyr Glu Val Cys Asp Ile Pro
65                  70                  75                  80
```

```
Gln Cys Ser Glu Val
                85
```

METHOD FOR NATIVE LIGATION OF POLYPEPTIDES

FIELD OF THE INVENTION

The present invention relates to a method for native ligation of polypeptides. The invention also relates to functionalized polypeptides useful for implementing this method for native ligation, as well as a method for manufacturing these functionalized polypeptides. The invention also relates to an amine compound as well as a functionalized resin, useful for implementing the method for manufacturing functionalized polypeptides.

TECHNICAL BACKGROUND

The synthesis of polypeptides by conventional solid-phase methods, amino acid by amino acid, is limited by low yields when the polypeptides synthesized are of large size. For overcoming this limitation, assembly of two polypeptides by chemical ligation, in order to produce a longer polypeptide, is known.

In general, it is desirable for the bond between the polypeptides assembled by ligation to be native, i.e. to correspond to the natural structure of the polypeptides.

Currently the main method for native ligation is that of Kent and Dawson, which is described for example in documents WO 96/34878 and WO 98/28434. This method is based on a chemoselective reaction between a (C-terminal) thioester peptide and a cysteinyl peptide. The main drawback of this method is that manufacture of the thioester peptides requires complex chemical processes.

An alternative method is so-called Staudinger ligation, described in documents WO 01/68565 and WO 01/87920. This comprises reaction of a phosphinothioester with an azide and hydrolysis of the combined reagents to form an amide bond. This method is difficult to apply on an industrial scale.

A third method, described in document WO 2007/037812, is based on reaction of an α-keto acid with an amine in a reaction of decarboxylative condensation. However, the keto acids are molecules that are difficult to manufacture and to incorporate in peptides. Moreover, this third method is difficult to apply in peptide synthesis laboratories that are not equipped with means for carrying out complex organic syntheses.

There is therefore a real need to develop a new method for native ligation of polypeptides, which is both effective and simpler to implement, including on an industrial scale.

SUMMARY OF THE INVENTION

The invention relates firstly to a method for manufacturing a polypeptide of formula:

$$X_1\text{—}X''\text{—}X_2 \quad (III)$$

$X_1$ and $X_2$ each representing a peptide fragment, and $X''$ representing an amino acid residue comprising a thiol function, said method comprising at least one step of ligation reaction between a polypeptide of formula:

$$X_1\text{—}N(CH_2CH_2SH)_2 \quad (I)$$

and a polypeptide of formula:

$$H\text{—}X''\text{—}X_2. \quad (II)$$

According to an embodiment, the ligation reaction is carried out by bringing a polypeptide of formula:

into contact with the polypeptide of formula (II), in the presence of at least one compound that reduces the disulphide bonds.

According to an embodiment, $X_2$ represents a peptide fragment of formula $$X_2{'}\text{—}(X_i{''}\text{—}X_i{'})_{i=3\ldots n} \quad (IV)$$

n being an integer greater than or equal to 3, each $X_i{''}$, for i an integer comprised between 3 and n, representing an amino acid residue comprising a thiol function, and each $X_i{'}$, for i an integer comprised between 2 and n, representing a peptide fragment; the method comprising, before the step of ligation reaction between the polypeptide of formula (I) and the polypeptide of formula (II), a succession of n−2 steps of ligation reaction, the j-th step of ligation reaction, for j an integer comprised between 1 and n−2, being a ligation reaction between a polypeptide of formula:

$$H\text{—}X_{n-j}{''}\text{—}X_{n-j}{'}\text{—}N(CH_2CH_2SH)_2 \quad (V)$$

in which the amine function and/or the thiol function of residue $X_{n-j}{''}$ is protected, and a polypeptide of formula:

$$H\text{—}(X_i{''}\text{—}X_i{'})_{i=(n-j+1)\ldots n} \quad (VI)$$

to form a polypeptide of formula:

$$H\text{—}(X_i{''}\text{—}X_i{'})_{i=(n-j)\ldots n} \quad (VII)$$

the polypeptide of formula (VII) undergoing deprotection of the thiol function of the residue $X_{n-j}{''}$ at the end of the ligation reaction.

According to an embodiment, one or more of the n−2 steps of ligation reaction between the polypeptide of formula (V) and the polypeptide of formula (VI) is carried out by bringing a polypeptide of formula:

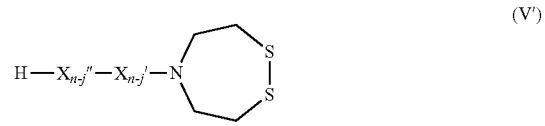

into contact with the polypeptide of formula:

$$H\text{—}(X_i{''}\text{—}X_i{'})_{i=(n-j+1)\ldots n} \quad (VI)$$

j being an integer comprised between 1 and n−2, in the presence of at least one compound that reduces the disulphide bonds.

The invention also relates to a method for manufacturing a cyclic polypeptide of formula:

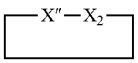

$X_2$ representing a peptide fragment, and $X''$ representing an amino acid residue comprising a thiol function, said method comprising at least one step of ligation reaction of a polypeptide of formula:

$$H-X''-X_2-N(CH_2CH_2SH)_2 \quad (XI)$$

with itself.

According to an embodiment, the ligation reaction is carried out by bringing a polypeptide of formula:

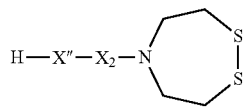

(XI')

into contact with at least one compound that reduces the disulphide bonds.

According to an embodiment of any one of the preceding methods, the ligation reaction or ligation reactions are carried out in an aqueous medium, preferably at a pH comprised between 6.5 and 8.5, more particularly preferably between 7 and 8, and ideally of approximately 7.5.

According to an embodiment of any one of the preceding methods, the ligation reaction or ligation reactions are carried out in the presence of at least one compound that reduces the disulphide bonds, selected from tris(2-carboxyethyl)phosphine, 4-mercaptophenylacetic acid, dithiothreitol, benzyl mercaptan and mixtures thereof.

The invention further relates to a polypeptide of formula:

$$X_1-N(CH_2CH_2SH)_2 \quad (I)$$

or of formula:

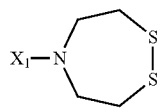

(I')

in which $X_1$ represents a peptide fragment.

According to an embodiment, $X_1$ comprises between 2 and 300 amino acid residues, preferably between 5 and 100 amino acid residues, more particularly preferably between 8 and 50 amino acid residues.

The invention also relates to a method for manufacturing a polypeptide of formula:

$$X_1-N(CH_2CH_2SH)_2 \quad (I)$$

$X_1$ representing a peptide fragment, comprising at least one step of peptide synthesis and one step of C-terminal functionalization.

According to an embodiment, the step of peptide synthesis precedes the step of functionalization; the step of peptide synthesis supplies a polypeptide of formula:

$$X_1-OH \quad (IX)$$

preferably comprising protective groups on its amine and carboxylic functions, with the exception of its C-terminal carboxylic function; and the step of functionalization comprises:

reaction of the polypeptide of formula (IX) with the amine compound of formula:

$$NH(CH_2-CH_2-S-G_1)_2 \quad (VIII)$$

in which $G_1$ represents a protective group, said protective group preferably forming a thioether, thioester or disulphide function, and more particularly preferably being the triphenylmethyl group, in the liquid phase, to form the polypeptide of formula (I);

optionally deprotection of the polypeptide of formula (I).

A subject of the invention is also a polymer resin support for solid-phase synthesis of polypeptides, comprising a main skeleton and NH—(CH$_2$CH$_2$—S-Trt-)$_2$ functional groups or NH—(CH$_2$CH$_2$—S-Trt-CO—NH—)$_2$ functional groups, where Trt represents a triphenylmethyl group optionally substituted with one or more substituents, in particular selected from the substituents chlorine, methoxy, methyl, fluorine and cyano; in which the NH—(CH$_2$CH$_2$—S-Trt-)$_2$ functional groups are bound to the main skeleton by the two triphenylmethyl groups, or the NH—(CH$_2$CH$_2$—S-Trt-CO—NH—)$_2$ functional groups are bound to the main skeleton by the two amine groups.

A subject of the invention is also a polymer resin support for solid-phase synthesis of polypeptides, comprising a main skeleton and G$_2$-AA-N—(CH$_2$CH$_2$—S-Trt-)$_2$ functional groups or G$_2$-AA-N—(CH$_2$CH$_2$—S-Trt-CO—NH—)$_2$ functional groups, where Trt represents a triphenylmethyl group optionally substituted with one or more substituents, in particular selected from the substituents chlorine, methoxy, methyl, fluorine and cyano; AA represents an amino acid residue optionally bearing one or more protective groups; G$_2$ represents a hydrogen atom or a protective group of amine function; in which the G$_2$-AA-N(CH$_2$CH$_2$—S-Trt-)$_2$ functional groups are bound to the main skeleton by the two triphenylmethyl groups or the G$_2$-AA-N—(CH$_2$CH$_2$—S-Trt-CO—NH—)$_2$ functional groups are bound to the main skeleton by the two amine groups.

According to an embodiment of the aforementioned polymer resin supports, the main skeleton is selected from the polystyrene, polyacrylamide, polyethylene glycol, cellulose, polyethylene, polyester, latex, polyamide, polydimethylacrylamide, polyethylene glycol-polystyrene copolymer, polyethylene glycol-polyacrylamide copolymer skeletons and derivatives thereof.

A subject of the invention is also a method for manufacturing a polymer resin support for solid-phase synthesis of polypeptides, comprising:

supplying a polymer resin;

functionalization of the polymer resin by reaction with the amine compound of formula:

$$NH(CH_2-CH_2-S-H)_2 \quad (VIII')$$

According to an embodiment of the method for manufacturing the polymer resin support, the method comprises, prior to the step of functionalization of the polymer resin:

supplying an amine compound of formula:

$$NH(CH_2-CH_2-S-G_1)_2 \quad (VIII)$$

in which $G_1$ represents a protective group, said protective group preferably forming a thioether, thioester or disulphide function, and more particularly preferably being the triphenylmethyl group;

deprotection of this amine compound to obtain the amine compound of formula (VIII').

According to an embodiment of the method for manufacturing the polypeptide of formula (I):

the step of functionalization precedes the step of peptide synthesis;

the step of functionalization comprises:

coupling an amino acid to a polymer resin support comprising a main skeleton and NH—(CH$_2$CH$_2$—S-Trt-)$_2$ functional groups or NH—(CH$_2$CH$_2$—S-Trt- CO—NH—)$_2$ functional groups, as described above, to supply a primer support; or supplying a primer support, which is a polymer resin support comprising a main skeleton and G$_2$-AA-N—(CH$_2$CH$_2$—S-Trt-)$_2$ functional groups or G$_2$-AA-N—(CH$_2$CH$_2$—S-Trt-CO—NH—)$_2$ functional groups, as described above;

the step of peptide synthesis comprises a succession of couplings of amino acids on the primer support.

According to an embodiment of this method, the coupling of an amino acid to the polymer resin support comprises bringing the polymer resin support into contact with an amino acid halide or with an amino acid and an activating agent, preferably selected from PyBOP, BOP, PyBROP, more particularly preferably PyBROP.

The invention also relates to a method for manufacturing a polypeptide of formula:

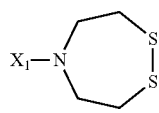
(I')

in which X$_1$ represents a peptide fragment, comprising a step of oxidation of a polypeptide of formula:

X$_1$—N(CH$_2$CH$_2$SH)$_2$ (I)

preferably in contact with air, or in the presence of I$_2$ or of diamide, and in a buffer, said oxidation step preferably being preceded by a step of manufacture of the polypeptide of formula (I) according to the method described above.

According to an embodiment of the method for manufacturing a polypeptide of formula (III) or (X), the latter comprises a step of manufacture of the polypeptide of formula (I) and/or (V) or (XI) which is according to the method for manufacturing the polypeptide of formula (I) described above, or a step of manufacture of the polypeptide of formula (I') and/or (V') or (XI') according to the method for manufacturing the polypeptide of formula (I') described above.

The invention also relates to a method for manufacturing a pharmaceutical composition comprising:

manufacturing a polypeptide according to the method for manufacturing a polypeptide of formula (III) or (X) described above, and formulating this polypeptide with one or more pharmaceutically acceptable adjuvants.

The invention also relates to a method for manufacturing a diagnostic device comprising:

manufacturing a polypeptide according to the method for manufacturing a polypeptide of formula (III) or (X) described above, and formulating this polypeptide in a form suitable for diagnostic use.

A subject of the invention is also an amine compound of formula:

NH(CH$_2$—CH$_2$—S-Trt)$_2$ (VIII")

where Trt represents the triphenylmethyl group.

The present invention makes it possible to overcome the drawbacks of the state of the art. More particularly it provides a method for native ligation of polypeptides, which is both effective and simpler to implement than the previous methods, including on an industrial scale.

This is achieved through the development of a reaction scheme in which a polypeptide modified at the C-terminal end with a bis(mercaptoethyl)amino group reacts with a polypeptide having a cysteine at the N-terminal end (or another amino acid comprising a thiol function) to form a native amide bond.

According to certain particular embodiments, the invention also has one or preferably several of the advantageous features listed below.

The method of ligation according to the invention optionally uses unprotected polypeptide reagents, in particular when a single ligation is carried out. The use of protected polypeptides is difficult owing to their low solubility, and because in addition it requires a step of deprotection after ligation, leading to an additional cost and the possibility of degradation. Conversely, the invention therefore makes it possible to avoid the drawbacks associated with protected polypeptides, in particular when a single ligation is carried out. The method according to the invention leads directly to the formation of a native bond at the point of ligation, without it being necessary to carry out deprotection after ligation.

The method of ligation according to the invention is based on the use of polypeptides modified with chemically stable functional groups, which are easy to introduce using conventional techniques of peptide synthesis.

The invention allows the use of proteinogenic amino acids for synthesis of the peptide fragments. Thus, there is no need to have recourse to the manufacture of amino acid derivatives (such as keto acids for example), which complicates the synthesis considerably.

Assembly of the polypeptide reagents can be carried out in standard fashion, for example using Fmoc/tert-butyl chemistry. Consequently, the method according to the invention is compatible with the automated industrial synthesis processes currently available. The amino acids and appropriate solid supports are currently available in large volume and at low cost.

The invention provides for ligation in an aqueous medium, which is therefore compatible with the solubility of the peptides and of the proteins.

The ligation reaction according to the invention can be carried out efficiently at a pH close to 7.5, i.e. under conditions compatible with complex polypeptides or proteins.

The ligation reaction according to the invention offers the possibility of self-ligation of a polypeptide, and therefore of manufacture of cyclic polypeptides.

DESCRIPTION OF EMBODIMENTS OF THE INVENTION

Figure 1:
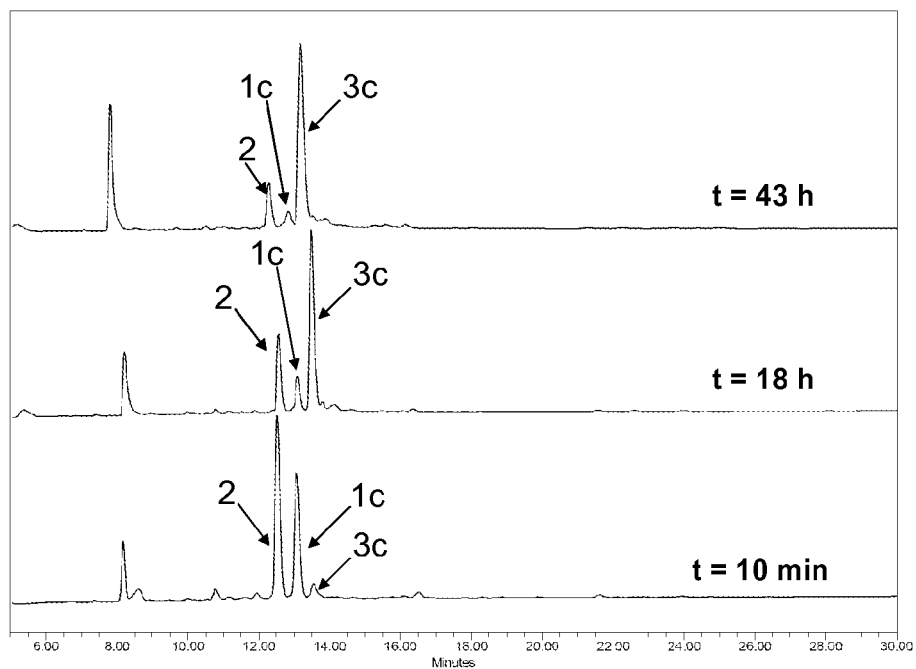
FIG. 1 shows the monitoring, by RP-HPLC (reverse-phase high-performance liquid chromatography), of native ligation between polypeptide 1c and polypeptide 2, to obtain polypeptide 3c, according to Example 7. The bottom plot corresponds to the time point t=10 min; the middle plot corresponds to the time point t=18 h; and the top plot corresponds to the time point t=43 h.

A more detailed, non-limitative description of the invention is presented below.

By "polypeptide" is meant, in the context of the present application, a linear chain of amino acid residues (greater than or equal to two in number) linked together by peptide bonds. The "polypeptides" within the meaning of the present application can therefore be for example oligopeptides, peptides or proteins according to the generally accepted definitions of these terms. The amino acid residues present in the polypeptides according to the invention can be selected from proteinogenic or non-proteinogenic amino acid residues. Preferably, they are selected from the twenty proteinogenic amino acid residues.

The notation of the polypeptides runs from the N-terminal end to the C-terminal end. The amino acid residues present along the polypeptide chain are designated according to the usual one-letter or three-letter code. An amino acid residue is a polypeptide fragment of formula —NH—(CH—R)—(C═O)—, in which R represents a side chain, different from one amino acid to the next.

By "peptide fragment" is meant, in the context of the present application, a portion of polypeptide comprising at least one amino acid residue. A peptide fragment, within the meaning of the present application, can therefore be for example: a sequence of amino acid residues (such as -AHG- or -Ala-His-Gly-) if the peptide fragment comprises neither the N-terminal end nor the C-terminal end of the polypeptide; or a sequence of amino acid residues having a group at its N-terminal end (such as H-AHG- or H-Ala-His-Gly-) if the peptide fragment comprises the N-terminal end of the polypeptide; or a sequence of amino acid residues having a group at its C-terminal end (such as -AHG-OH or -Ala-His-Gly-OH) if the peptide fragment comprises the C-terminal end of the polypeptide.

Native Ligation of Polypeptides

The invention provides a method for native ligation of polypeptides, according to which a polypeptide of formula:

$$X_1\text{—}N(CH_2CH_2SH)_2 \qquad (I)$$

reacts with a polypeptide of formula:

$$H\text{—}X''\text{—}X_2 \qquad (II)$$

to supply a polypeptide of formula:

$$X''\text{—}X_2. \qquad (III)$$

The polypeptide of formula (I) comprises a peptide fragment $X_1$ (said peptide fragment comprising the N-terminal end of the polypeptide) and a functional group —$N(CH_2CH_2SH)_2$ at the C-terminal end (bound to the (C═O) termination of the amino acid residue in C-terminal position).

The peptide fragment $X_1$ is of the form $Y_1$-$AA_1AA_2$ . . . $AA_n$. $Y_1$ is an N-terminal group, preferably a hydrogen atom, but optionally also any group substituting for the primary or secondary amines known to a person skilled in the art, for example an acyl group and in particular an acetyl group. n is an integer greater than or equal to 2. Each $AA_i$ represents an amino acid residue.

An example of a polypeptide of formula (I) is polypeptide 1 a (see Example 3 below) of formula:

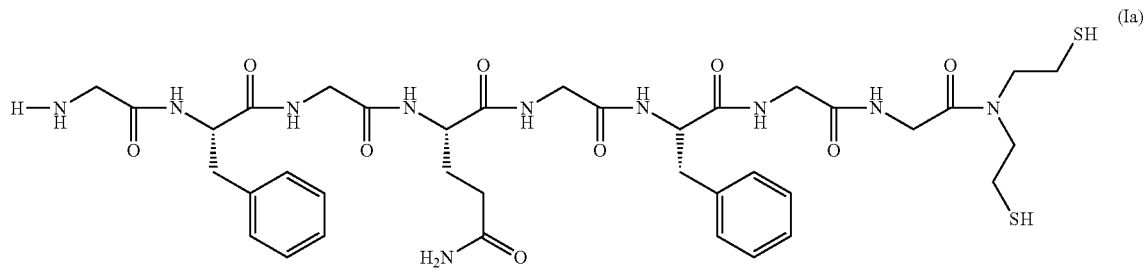

In this example, the peptide fragment $X_1$ is H-GFGQG-FGG.

The polypeptide of formula (I) preferably comprises between 2 and 300 amino acid residues, preferably between 5 and 100 amino acid residues, more particularly preferably between 8 and 50 amino acid residues.

The polypeptide of formula (II) comprises a hydrogen atom and a residue X" at the N-terminal end. The residue X" is an amino acid residue comprising a thiol function. This thiol function can in particular be a beta-amino thiol function (in which case the residue X" preferably represents the cysteine residue) or a gamma-amino thiol function (in which case the residue X" preferably represents the homocysteine residue).

Throughout the description which follows, according to a particular embodiment, X" can be read as representing a cysteine residue (Cys).

According to the notation used above, $X_2$ represents a peptide fragment, which comprises the C-terminal end of the polypeptide of formula (II) as well as all of the amino acid residues of this polypeptide, except the N-terminal residue.

The peptide fragment $X_2$ is of the form $AA_2'AA_3'$ . . . $AA_n'$-$Y_2$. $Y_2$ is an end group, preferably an —OH or —$NH_2$ group or an —OR or —NRR' group, R and R' each representing an alkyl or aryl group. n is an integer greater than or equal to 2. Each $AA_i'$ represents an amino acid residue.

The polypeptide of formula (II) preferably comprises between 2 and 300 amino acid residues, preferably between 5 and 100 amino acid residues, more particularly preferably between 8 and 50 amino acid residues.

The polypeptide of formula (II) can for example be obtained by a usual method of peptide synthesis, in particular a method of solid-phase synthesis. It can also be obtained by means of a preceding native ligation (see below).

Each of the polypeptides of formula (I) and (II) preferably comprises only amino acid residues selected from the twenty proteinogenic amino acid residues. However, according to a particular embodiment, the polypeptides of formula (I) and (II) comprise one or more non-proteinogenic amino acid residues.

The amino acid residues of the polypeptides of formula (I) and (II) can optionally be protected by groups protecting the side chains.

For the ligation reaction to take place correctly, the presence of the two free thiol groups on the polypeptide of formula (I) is essential. The ligation is said to be native because the peptide fragment $X_1$ is linked to the peptide fragment $X''$—$X_2$ by an amide bond.

It is possible to carry out the above ligation reaction by bringing the polypeptide of formula (II) into contact with a polypeptide of formula:

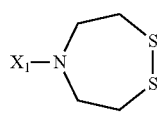
(I')

provided that a compound that reduces the disulphide bonds, which can preferably be a thiol compound such as 4-mercaptophenylacetic acid (MPAA), dithiothreitol (DTT), thiophenol (and derivatives thereof), an alkylthiol (in particular benzyl mercaptan) or a phosphine such as tris(2-carboxyethyl)phosphine (TCEP), is used during the reaction. The combined use of several of these compounds is also appropriate, for example the use of MPAA and TCEP.

In fact, the polypeptide of formula (I') is then reduced in situ and supplies the polypeptide of formula (I) for the ligation reaction.

In general, the ligation reaction starting from the polypeptide of formula (I') as reagent can be more practical to implement than the ligation reaction directly with the polypeptide of formula (I). In fact, the polypeptide of formula (I) has a natural tendency to oxidize to the polypeptide of formula (I'), in particular under the action of the oxygen of the air. For example, it is possible for the polypeptide of open form (I) to oxidize over time when it is stored in lyophilized form. In other words, a preparation of the polypeptide of formula (I) generally partly contains, inevitably, the polypeptide of formula (I'). The presence of these two forms may complicate characterization and purification. That is why it may be simpler to implement the ligation reaction by bringing the polypeptide of formula (I') into contact with the polypeptide of formula (II), the polypeptide with cyclic termination of formula (I') being reduced in situ to the open polypeptide of formula (I).

For the same reasons, even when the ligation reaction is carried out directly by bringing the polypeptide of formula (I) into contact with the polypeptide of formula (II), it is preferable if one or more of the aforementioned compounds that reduce the disulphide bonds are used during the reaction.

Preferably, MPAA, when it is present, is used at a concentration comprised between 1 and 500 mM, for example at a concentration of approximately 200 mM during the reaction.

Preferably, TCEP, when it is present, is used at a concentration comprised between 1 and 200 mM, for example at a concentration of approximately 80 mM during the reaction.

In the case where the N-terminal amino acid residue of polypeptide (I) comprises a thiol function, the latter must be protected during ligation, otherwise there will be a competing reaction of cyclization of the polypeptide of formula (I). Alternatively, the alpha amine function can be protected in order to avoid the cyclization reaction. It is possible for example to use protection of the thiazolidine type, which protects the thiol and the alpha amine simultaneously.

The ligation reaction preferably takes place in the liquid phase, and in particular in an aqueous medium, for example in a phosphate buffer. Preferably, this reaction is carried out at a pH comprised between 6.5 and 8.5, more particularly preferably at a pH comprised between 7 and 8 and ideally at a pH close to 7.5.

The ligation reaction is preferably carried out at a temperature comprised between 0 and 50° C., and ideally at a temperature of approximately 37° C. The reaction time is adjusted depending on the choice of reagents and other reaction conditions. The appropriate time can also be adjusted according to the results of liquid chromatography—mass spectrometry analysis during the reaction. The appropriate time will typically be from a few hours to a few days.

Each of the polypeptides of formula (I) and (II) is preferably present at a concentration comprised between 0.01 and 50 mM, during the reaction. The ratio of molar concentration between the polypeptides of formula (I) and II) during the reaction is preferably comprised between 2:3 and 3:2.

The ligation reaction described above can be followed by a step of purification of the polypeptide of formula (III) obtained, for example by liquid chromatography or by any other usual technique.

Production of a Polypeptide with Several Successive Native Ligations

The invention also makes it possible to produce polypeptides using a succession of several ligation reactions as described above. This may prove appropriate for obtaining large polypeptides, for example polypeptides comprising more than approximately 100 amino acid residues. In fact, in such cases the manufacture of polypeptides of formulae (I) and (II) by direct synthesis may have a low yield, and it is therefore advantageous to use two or more than two successive ligations, so that only polypeptides comprising for example less than approximately 50 amino acid residues have to be synthesized directly.

As an example, the use of two successive ligations makes it possible to obtain a polypeptide comprising approximately 150 amino acid residues without requiring direct synthesis of polypeptides comprising more than approximately 50 amino acid residues; the use of three successive ligations makes it possible to obtain a polypeptide comprising approximately 200 amino acid residues without requiring direct synthesis of polypeptides comprising more than approximately 50 amino acid residues.

Thus, the method according to the invention makes it possible to obtain a polypeptide of formula (III) in which the peptide fragment $X_2$ is of the form $X_2'$—$X_3''$—$X_3'$— . . . $X_n''$—$X_n'$ (n being an integer greater than or equal to 3; each $X_i'$, for i an integer between 2 and n, being a peptide fragment; and each $X_i''$, for i an integer between 3 and n, being a residue $X''$, i.e. an amino acid residue comprising a thiol function, and in particular a cysteine residue according to a particular embodiment) using n−1 successive ligations. In other words the polypeptide obtained has in this case the formula:

$$X_1-X''-X_2'-X_3''-X_3'-\ldots X_n''-X_n' \quad (III')$$

The first ligation reaction involves on the one hand a polypeptide of formula $$H-X_{n-1}''-X_{n-1}'-N(CH_2CH_2SH)_2 \quad (Va)$$

and on the other hand a polypeptide of formula $$H-X_n''-X_n'. \quad (VIa)$$

This ligation reaction is exactly the same as that described in the previous section. It leads to production of the polypeptide of formula $$H-X_{n-1}''-X_{n-1}'-X_n''-X_n'. \quad (VIb)$$

The thiol function or the N-terminal amine function (or the thiol function and the amine function) of the amino acid residue $X_{n-1}''$ must be protected in the polypeptide of formula (Va) during ligation, otherwise there will be a competing reaction of cyclization of the polypeptide of formula (Va). Protection of the thiazolidine type, for example, can be used for this.

At the end of the ligation reaction, the thiol function of the amino acid residue $X_{n-1}''$ must be deprotected in the polypeptide of formula (VIb) in order to allow the following ligation reaction.

The second ligation reaction involves on the one hand a polypeptide of formula:

$$H-X_{n-2}''-X_{n-2}'-N(CH_2CH_2SH)_2 \quad (Vb)$$

and on the other hand the polypeptide of formula (VIb) obtained previously. The thiol function of the amino acid residue $X_{n-2}''$ must be protected in the polypeptide of formula (Vb), otherwise there will be a competing reaction of cyclization of the polypeptide of formula (Vb). Protection of the thiazolidine type, for example, can be used for this. The reaction of ligation of the polypeptide of formula (Vb) with the polypeptide of formula (VIb) is then followed by deprotection of the thiol function of the amino acid residue $X_{n-2}''$ prior to the following ligation reaction.

The following ligation reactions are of the same type. Generally, ligation reaction number j (for j an integer comprised between 1 and n−2) involves a polypeptide of formula $$H-X_{n-j}''-X_{n-j}'-N(CH_2CH_2SH)_2 \quad (V)$$

and a polypeptide of formula:

$$H-(X_i''-X_i')_{i=(n-j+1)\ldots n} \quad (VI)$$

to form a polypeptide of formula:

$$H-(X_i''-X_i')_{i=(n-j)\ldots n} \quad (VII)$$

Finally, the last (i.e. the n−1$^{th}$) ligation reaction involves the polypeptide of formula:

$$X_1-N(CH_2CH_2SH)_2 \quad (I)$$

and the polypeptide of formula:

$$H-X''-X_2, \quad (II)$$

which represents here $H-X''-X_2'-X_3''-X_3'-\ldots -X_n''-X_n'$, to form the polypeptide of formula:

$$X_1-X''-X_2, \text{ i.e.} \quad (III)$$

$$X_1-X''-X_2'-X_3''-X_3'\ldots -X_n''-X_n' \quad (III')$$

Each successive ligation reaction can be carried out as described in the section "native ligation of polypeptides". In particular, it may be advantageous to carry out the ligation reaction number j (for j an integer comprised between 1 and n−2) by bringing the polypeptide of formula (VI) into contact with the polypeptide of formula:

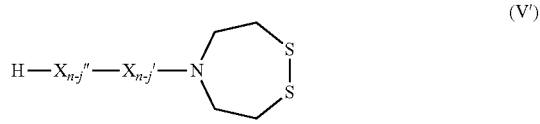

in the presence of one or more of the aforementioned compounds that reduce disulphide bonds, the polypeptide of formula (V') then being reduced in situ and supplying the polypeptide of formula (V) for the ligation reaction.

Production of a Cyclic Polypeptide By Native Self-Ligation

The principles used for native ligation described above can also be used for producing cyclic polypeptides, by native self-ligation of a polypeptide (ligation of one end of the polypeptide with the other end of the same polypeptide). In general, the invention thus proposes a method for manufacturing a cyclic polypeptide of formula:

where $X_2$ represents a peptide fragment, and X" represents an amino acid residue comprising a thiol function, by a reaction of ligation of a polypeptide of formula:

$$H-X''-X_2-N(CH_2CH_2SH)_2 \quad (XI)$$

with itself.

The polypeptide of formula (XI) preferably comprises between 2 and 300 amino acid residues, preferably between 5 and 100 amino acid residues, more particularly preferably between 8 and 50 amino acid residues.

The polypeptide of formula (XI) comprises a hydrogen atom and a residue X" at the N-terminal end, X" having the meaning given above. $X_2$ represents in this case a peptide fragment of the form $AA_1 AA_2 \ldots AA_n$ where n is an integer greater than or equal to 1 and each $AA_i$ represents an amino acid residue.

The polypeptide of formula (XI) preferably comprises only amino acid residues selected from the twenty proteinogenic amino acid residues.

However, according to a particular embodiment, the polypeptide of formula (XI) comprises one or more non-proteinogenic amino acid residues.

The amino acid residues of the polypeptide of formula (XI) can optionally be protected by groups protecting the side chains.

It is possible to carry out the above ligation reaction by bringing the polypeptide of formula (XI'):

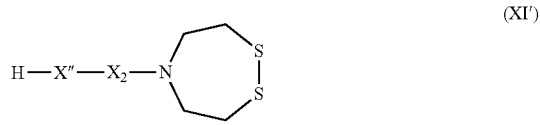

into contact with at least one compound that reduces the disulphide bonds, which is preferably as described above. In fact, the polypeptide of formula (XI') is then reduced in situ and supplies the polypeptide of formula (XI) for the ligation reaction.

In general, even when the ligation reaction is carried out directly starting from the polypeptide of formula (XI), it is preferable if one or more of the aforementioned compounds that reduce the disulphide bonds are used during the reaction.

In general, cyclization of the polypeptide of formula (XI) is unaffected by competing multimerizations, if the reaction is carried out in sufficiently dilute conditions. It is possible for example to use a concentration of polypeptide of formula (XI) comprised between 0.01 and 50 mM, typically of approximately 1 mM (or optionally between 0.01 and 0.1 mM if there is a serious risk of multimerizations).

Moreover, the preferred conditions of implementation of the ligation reaction are the same as those described above for the reaction starting from the polypeptides of formula (I) and (II).

The ligation reaction described above can be followed by a step of purification of the cyclic polypeptide of formula (X) obtained, for example by liquid chromatography or by any other usual technique.

Method for Manufacturing the Polypeptides of Formula (I), (V) and (XI)

The polypeptides of formula (I), (V) and (XI) are compounds that are useful for implementation of the ligation reaction described above. A subject of the invention is therefore also these polypeptides of formula (I) (or of formula (V) or (XI)) as such, as well as a method by which they can be manufactured.

The method for manufacturing the polypeptides of formula (I) (or of formula (V) or (XI)) involves two main steps:
    a step of peptide synthesis; and
    a step of C-terminal functionalization.

The invention provides two main variants of this method. According to the first variant, peptide synthesis precedes functionalization. According to the second variant, peptide synthesis follows functionalization. The second variant makes it possible to obtain a higher yield and is simpler to implement on an industrial scale.

According to the first variant, the first step (step of peptide synthesis) makes it possible to obtain the polypeptide of formula:

$$X_1\text{—OH} \tag{IX}$$

This step of peptide synthesis can be carried out according to any method known to a person skilled in the art. It can in particular be carried out in the liquid phase or, preferably, in the solid phase.

Schematically, the peptide synthesis comprises a succession of couplings of amino acids starting from a primer (initial amino acid or peptide fragment resulting from previous additions of amino acids) and deprotections. More precisely, the peptide synthesis can comprise successively:
    (a) supply of a peptide fragment having an unprotected N-terminal end, and of an amino acid protected at its N-terminal end;
    (b) establishment of a peptide bond between the amino acid and the peptide fragment, at the N-terminal end of said peptide fragment;
    (c) deprotection of the N-terminal end of the bound amino acid, to supply the peptide fragment of the following step (a).

In the case of solid-phase peptide synthesis, the peptide fragment (primer) is bound to a solid support at its C-terminal end. The solid support is preferably a polymer in the form of insoluble or soluble particles (beads). It is possible for example to use resins based on polystyrene, polyacrylamide, polyethylene glycol, cellulose, polyethylene, polyester, latex, polyamide, polydimethylacrylamide and resins derived therefrom. It is also possible to use a silica gel or glass beads as solid support.

The peptide fragment and the solid support are linked together via an appropriate functional group, called a "linker". Thus, firstly, the amino acid corresponding to the C-terminal end of the polypeptide to be synthesized is fixed on the linker functional groups of the solid support (protecting the amine function of the amino acid during coupling and then deprotecting it to make it available for the following reaction), which constitutes the first primer, then the following amino acids are added according to the succession of reactions mentioned above.

In the course of the various coupling reactions, it is advantageous to use an activating compound, in particular a carbodiimide (for example dicyclohexylcarbodiimide or diisopropylcarbodiimide) in the presence of a triazole (for example 1-hydroxy-benzotriazole or 1-hydroxy-7-azabenzotriazole), or a phosphonium or uronium salt of a non-nucleophilic anion (for example HBTU, HATU, TBTU or PyBOP); or to use activated amino acids in the form of acid halides, for example acid fluorides.

In the case of a solid-phase synthesis, and once the last amino acid coupling reaction has been carried out, a reaction of separation (or cleavage) of the polypeptide from its solid support is provided for.

In the course of the different coupling reactions, the N-terminal ends of the amino acids are advantageously protected by a protective group, preferably an Fmoc group (9H-fluoren-9-ylmethoxycarbonyl) or a t-Boc group (tert-butoxycarbonyl) or NSC group (2-(4-nitrophenylsulphonyl)ethoxycarbonyl).

Similarly, the side chains of the amino acid residues are preferably protected during the various coupling reactions by one or more suitable protective groups, for example a tert-butyl group for the chains comprising a carboxylic function.

In this case, once the last amino acid coupling reaction has been carried out, a reaction of deprotection of the side chains can be provided for. It should, however, be noted that it may be preferable to keep all of the protections (apart from an optional protection of the COOH function at the C end) with a view to the functionalization step.

At the end of the step of peptide synthesis, the polypeptide of formula (IX) is functionalized.

The functionalization step comprises successively:
    Optionally protection of the N-terminal end of the polypeptide of formula (IX) with a protective group, preferably selected from the family of the carbamates, amides or alkyl groups, and in particular a tert-butoxycarbonyl (t-Boc), Fmoc (9H-fluoren-9-ylmethoxycarbonyl), trifluoroacetyl or triphenylmethyl group.
    Also optionally, protection of the functions of the side chains of the amino acid residues of the polypeptide of formula (IX), and quite particularly of the amine functions (preferably by means of the above protective groups) and of the carboxylic functions (for example by means of tert-butyl groups).
    Alternatively, and according to a simpler embodiment, the polypeptide of formula (IX) can be supplied directly in a form in which all of the amine and carboxylic functions are protected, by providing selective deprotection of the COOH function of the C-terminal end.
    Coupling of the polypeptide of formula (IX) with an amine compound of formula:

$$NH(CH_2\text{—}CH_2\text{—}S\text{-}G_1)_2 \tag{VIII}$$

$G_1$ being a protective group.

Optionally deprotection of the polypeptide.

Regarding the amine compound of formula (VIII), $G_1$ is preferably selected from the groups supplying a thioether, thioester (for example acetyl) or disulphide (for example tert-butylsulphenyl) function. More particularly preferably, $G_1$ is the triphenylmethyl group. In this case, the amine compound is bis({2-[triphenylmethyl)sulphanyl]ethyl})amine. Regarding a method of preparation of the amine compound of formula (VIII), reference may be made to Example 1 below.

An activator is advantageously present during the coupling reaction, for example benzotriazol-1-yl-oxytripyrrolidinophosphonium hexafluorophosphate (PyBOP) or bromotrispyrrolidinophosphonium hexafluorophosphate (PyBROP) or the C-terminal amino acid itself activated in the form of a halogenated derivative (in particular in the form of an amino acid fluoride or amino acid chloride), and the latter can be preformed or formed in situ using suitable reagents known to a person skilled in the art. Among the halides of amino acids, the amino acid fluorides are preferred, preformed by reaction with 1,3,5-trifluorotriazine or formed in situ with the aid of TFFH (tetramethylfluoroformamidinium hexafluorophosphate).

In general, any reagent allowing activation of the carboxylic acid function of the amino acid known to a person skilled in the art can also be envisaged, such as HBTU, TBTU, HATU, BOP, etc. (reference may be made for example to *Chemical approaches to the synthesis of peptides and proteins* by Lloyd-Williams, P., Albericio, F., Giralt, E., 1997, CRC Press). PyBOP, PyBROP, BOP or more generally the phosphoniums are preferred.

At the end of the functionalization step, the polypeptide of formula (I) is obtained. It is advantageous at this stage to provide a step of purification of the compound, for example by liquid chromatography.

According to the second variant of the method for producing a polypeptide of formula (I), the functionalization step precedes the step of peptide synthesis. This second variant is applied in the solid phase. Thus, the functionalization step consists, in this embodiment, of creating a primer solid support from a previously functionalized solid support.

A soluble or insoluble polymer is used as solid support, the insoluble polymer preferably being in the form of particles (beads). For example, it is possible to use a resin based on polystyrene (preferably) or based on polyacrylamide, polyethylene glycol, cellulose, polyethylene, polyester, latex, polyamide, polydimethylacrylamide, polyethylene glycol-polystyrene copolymer, polyethylene glycol-polyacrylamide copolymer or a resin derived therefrom.

Moreover, the solid support has linker groups, which are preferably chloro-triphenylmethyl (or chlorotrityl) groups, where the triphenylmethyl is optionally substituted with one or more substituents, in particular selected from the substituents chlorine, methoxy, methyl, fluorine and cyano.

As examples of solid support, polystyrene resins having trityl chloride, 2-chlorotrityl chloride, 4-methyltrityl chloride or 4-methoxytrityl chloride linker groups may be mentioned. Solid supports of this kind are available commercially, for example from Glycopep.

According to another embodiment, the solid support has linker groups that are groups of the trityl-alcohol type, i.e. OH-Trt-CO—NH— groups, where the triphenylmethyl (Trt) is optionally substituted with one or more substituents, in particular selected from the substituents chlorine, methoxy, methyl, fluorine and cyano. Solid supports having such linker groups are described for example in Quibell, JACS 1995, 117, 11656-11668, and are available commercially, for example in the ChemMatrix® range of polyethylene glycol solid supports.

The use of solid supports of this type requires a preliminary step of activation of the solid support:
- either with a brominated agent (in particular acetyl bromide) for modifying the linker groups in the form Br-Trt-CO—NH—;
- or with a chlorinated agent (in particular oxalyl chloride) for modifying the linker groups in the form Cl-Trt-CO—NH—.

An activation step of this type is described for example in Harre et al., Reactive & Functional Polymers 1999, 41, 111-114.

Alternatively, the resin can be reacted directly with the amine $NH(CH_2-CH_2-SH)_2$ in the presence of $BF_3.Et_2O$, according to Singh, S. et al., J. Org. Chem. 2004, 69, 4551-4554.

The use of solid supports of this type may make it possible to use skeletons of resin of the polyethylene glycol or polyethylene glycol-polystyrene type, which are more suitable for preparing long polypeptides than the resins of the polystyrene type.

Preferably, the particles have a Dv50 comprised between 1 and 1000 μm. Dv50 is defined as the 50th percentile of the particle size distribution, i.e. 50% of the particles have a size below Dv50 and 50% have a size above Dv50. In general, Dv50 is characteristic of the granulometric profile (volumetric distribution) of the particles, and it can be determined by laser granulometry (for a size below 200 μm), or by sieving (for a size above 200 μm).

The functionalized solid support is prepared by coupling the amine compound of formula:

$$NH(CH_2-CH_2-SH)_2 \quad (VIII')$$

to the aforementioned solid support. The amine compound (VIII') can itself be obtained by deprotection of the amine compound of the above formula (VIII), in which $G_1$ is a protective group.

Coupling is carried out in an acid medium in order to limit the risks of unmasking the secondary amine, which would lead to secondary reactions.

The trityl chloride groups in excess are preferably neutralized, for example with methanol. It is then important to add a base to neutralize the HCl formed.

It can be provided that preparation of the functionalized solid support forms an integral part of the second variant of the method for manufacturing the polypeptides of formula (I). Alternatively, the functionalized solid support can be prepared in advance and separately, so as to be ready for use in the context of the second variant of the method for manufacturing the polypeptides of formula (I).

The functionalized solid support is a polymer resin support that comprises a main skeleton (of polystyrene, polyethylene glycol-polystyrene, polyacrylamide, polyethylene glycol, cellulose, polyethylene, polyester, latex, polyamide, polydimethylacrylamide, polyethylene glycol-polystyrene copolymer, polyethylene glycol-polyacrylamide copolymer type or a derivative thereof, as required) and NH—$(CH_2CH_2-S-Trt-)_2$ groups bound to the main skeleton by the two Trt groups, or NH—$(CH_2CH_2-S-Trt-CO-NH-)_2$ groups, bound to the main skeleton by the two NH functions, in the case when the starting solid support is of the trityl-alcohol type.

In the above, Trt represents a triphenylmethyl group optionally substituted with one or more substituents in particular selected from the substituents chlorine, methoxy, methyl, fluorine and cyano.

Thus, this polymer resin support is essentially devoid of free thiol functions, and has secondary amine functions (disulphanylethylamine functions).

Then, an amino acid is coupled to the functionalized solid support.

Preferably the amino acid is protected at its N-terminal end by a protective group that is labile in the presence of a base, preferably selected from the 2-(4-nitrophenylsulphonyl) ethoxycarbonyl (NSC) group or Fmoc.

Preferably, the amino acid comprises protective groups on some or all (preferably all) of the functions present on its side chain, and in particular the carboxylic, amine, alcohol, phenol, guanidine (for arginine) and imidazole (for histidine) functions. Protective groups of this kind are known to a person skilled in the art. Reference may be made for example to the reference work *Protective groups in organic synthesis*, 2nd edition, T. Greene and P. Wuts, John Wiley & Sons, Inc.

Preferably, the amino acid is activated in the presence of PyBOP or of BOP or more particularly preferably in the presence of PyBROP, or in the form of a halide, in particular fluoride (i.e. a fluorine atom is bound to the acyl group of the amino acid residue).

The amino acid reacts with the secondary amine function present on the functionalized solid support to form an amide bond. After coupling of the amino acid, deprotection of the latter can optionally be carried out.

Consequently, at the end of the functionalization step, a polymer resin support is obtained, a so-called primer support, comprising $G_2$-NH—CHR—CO—N(CH$_2$CH$_2$—S-Trt-)$_2$ groups (R representing an amino acid side chain), which can also be designated $G_2$-AA-N(CH$_2$CH$_2$—S-Trt-)$_2$ (AA representing an amino acid residue), these groups being bound to the main skeleton by the two Trt groups; or $G_2$-AA-N—(CH$_2$CH$_2$—S-Trt-CO—NH—)$_2$ groups, bound to the main skeleton by the two NH functions.

It will be recalled that Trt denotes a triphenylmethyl group optionally substituted with one or more substituents in particular selected from the substituents chlorine, methoxy, methyl, fluorine and cyano. Moreover, $G_2$ represents a hydrogen atom or an amine function protecting group, depending on whether or not the alpha amine group of the amino acid has been deprotected. Finally, the functions of the side chain R of the amino acid residue AA can advantageously be protected, as mentioned above.

The primer support thus obtained (with or without protective groups) is also an object of the invention as such.

Then the step of peptide synthesis is carried out, similarly to what was described above in relation to the first embodiment, the initial primer being supplied by the amino acid coupled to the activated support.

Once the last amino acid coupling reaction has been carried out, a reaction of separation (or cleavage) of the polypeptide from its solid support is provided, and if necessary the appropriate deprotections, after which the polypeptide of formula (I) is obtained. Just as for the first variant, it is advantageous at this stage to provide a step of purification of the compound, for example by liquid chromatography.

Method for Manufacturing the Polypeptides of Formula (I'), (V') and (XI')

The polypeptides of formula (I'), (V') and (XI') mentioned above can be obtained very easily starting from the polypeptides of formula (I), (V) and (XI) respectively by oxidation in the air, for example in an ammonium bicarbonate buffer at approximately pH 8. Another advantageous possibility consists of using iodine $I_2$ or the diamide $H_2NCO$—N=N—$CONH_2$.

Applications

The polypeptides of formula (I) obtained according to the invention can be used for producing a bank of polypeptides, for example for screening purposes.

They can also be used for manufacturing pharmaceutical compositions, in combination with one or more pharmaceutically acceptable additives (including one or more pharmaceutically acceptable vehicles). As examples of pharmaceutical compositions that can be obtained according to the invention, medicinal products and vaccine preparations may be mentioned.

They can also be used for producing diagnostic kits.

EXAMPLES

The following examples illustrate the invention without limiting it.

Example 1 relates to preparation of the compound bis({2-[triphenylmethyl)sulphanyl]ethyl})amine (compound of formula (VIII)).

Examples 2 and 3 lead to the manufacture of a polypeptide 1a of formula H-GFGQGFGG-N(CH$_2$CH$_2$SH)$_2$ (SEQ ID NO: 1, corresponding to general formula (I) above) according to the first variant of the method for manufacturing a polypeptide of formula (I), described above (liquid-phase synthesis).

Examples 4 and 5 lead to the manufacture of a functionalized resin, having disulphanylethylamine functions.

Example 6 relates to preparation of a so-called "primer" support from the aforementioned functionalized resin, on which a first amino acid is fixed.

Example 7 relates to preparation of the polypeptides 1c (H-ILKEPVHGG-N(CH$_2$CH$_2$SH)$_2$) (SEQ ID No: 2), 1d (H-ILKEPVHGA -N(CH$_2$CH$_2$SH)$_2$) (SEQ ID NO: 3), 1e (H-ILKEPVHGV-N(CH$_2$CH$_2$SH)$_2$) (SEQ ID NO: 4) and 1f (H-ILKEPVHGY-N(CH$_2$CH$_2$SH)$_2$) (SEQ ID NO: 5), compounds corresponding to general formula (I) above, according to the second variant of the method for manufacturing a polypeptide of formula (I), described above (solid-phase synthesis).

Example 8 relates to ligation of the respective polypeptides 1 c, 1d and 1f with a polypeptide 2 of formula H-CILKEPVHGV-NH$_2$ (SEQ ID NO: 6) corresponding to general formula (II), to supply respective polypeptides 3c (SEQ ID NO: 9), 3d (SEQ ID NO: 10) and 3f (SEQ ID NO: 11).

Example 9 relates to the synthesis of polypeptide 1g (H-CHHLEPGG-N(CH$_2$CH$_2$SH)$_2$) (SEQ ID NO: 7), a compound corresponding to general formula (XI) above, according to the second variant of the method for manufacturing a polypeptide of general formula (XI), described above (solid-phase synthesis); as well as cyclization of this polypeptide to supply a cyclic polypeptide corresponding to general formula (X) above.

Example 10 relates to oxidation of the polypeptides 1c, 1d, 1e and 1f to dithiazepanes (compounds corresponding to general formula (I') above).

Example 11 relates to the ligation of polypeptide 1c with a polypeptide 4 (SEQ ID NO: 17) having an N-terminal homocysteine, to supply a polypeptide 5 (SEQ ID NO: 18).

Examples 12, 13 and 14 relate respectively to the synthesis of a polypeptide 6 (SEQ ID NO: 19), a polypeptide 7 (SEQ ID NO: 20) and a polypeptide 8 (SEQ ID NO: 21).

Example 15 relates to the ligation of polypeptide 7 and of polypeptide 8 to form a polypeptide 7-8 (SEQ ID NO: 22), and Example 16 relates to the ligation of polypeptide 6 with polypeptide 7-8 to form a polypeptide 6-7-8 (SEQ ID NO: 23) after deprotection of the thiazolidine present on the N-terminal cysteine of fragment 7-8. This is therefore a construction with two successive ligations. The final polypeptide 6-7-8 is a linear polypeptide of sequence: H-IRNCI-IGKGRSYKGTVSITKSGI KCQPWSSMIPHEHS-FLPSSYRGKDLQENYCRNPRGEEGGPWCFTSNPEV RYEVCDIPQCSEV-NH$_2$, the cysteines shown in bold being those involved in the ligations.

Example 1

Preparation of bis({2-[triphenylmethyl)sulphanyl]ethyl})amine 1.50 g of bis(2-chloroethyl)amine (8.4 mmol) and 4.65 g of triphenylmethanethiol (2 equivalents, 16.80 mmol) are introduced into a flask and placed under inert atmosphere. With magnetic stirring, 25 mL of anhydrous dimethylformamide (DMF) is added and the reaction mixture is cooled down in an ice bath. 4 equivalents of 1,8-diazabicyclo[5.4.0]undec-7-ene (DBU) are added dropwise to the mixture. The mixture is left under stirring at ambient temperature for 3 hours and the reaction is monitored by thin-layer chromatography (TLC) (eluent: cyclohexane/ethyl acetate/triethylamine:8/2/0.1). After this time, the solvent is evaporated in a rotary evaporator. The white solid obtained is then dissolved in 50 mL of dichloromethane (DCM) and the product is extracted three times with a 5% aqueous solution of KH$_2$PO$_4$. The product is then purified by silica gel column chromatography (eluent: cyclohexane/EtOAc/triethylamine (TEA):8/2/0.1), obtaining 1.46 g of white amorphous solid (yield: 28%)

The analysis of the product is as follows.

Rf=0.37 (silica gel, cyclohexane/EtOAc/TEA:8/2/0.1); $^1$H NMR (300 MHz, CDCl$_3$) δ 7.41-7.37 (m, 12H, Trt), 7.15-7.29 (m, 18H, Trt), 2.23-2.36 (m, 8H, CH$_2$), 1.26 (s, 1H, NH); $^{13}$C (75 MHz, CDCl$_3$) 154.1; 129.8; 128.1; 126.9; 47.9; 32.6; MALDI-TOF: 243.1 [Trt$^+$], 622.3 [M+H$^+$]$^+$, 644.3 [M$^+$+Na$^+$].

Example 2

Synthesis of the Polypeptide H-GFGQGFGG-OH (SEQ ID NO: 8)

1 g of Wang resin (charge: 1.1 mmol/g) is put in a reactor and solvated for 30 min in DMF. In parallel, in a flask under inert atmosphere, 3.27 g of Fmoc-Gly-OH (10 equivalents, 11 mmol) is dissolved in 100 mL of anhydrous dichloromethane/DMF mixture (99/1, v/v). A solution of 857 μL of diisopropyl carbodiimide (5 equivalents, 5.50 mmol) in 5 mL of anhydrous dichloromethane is added, under inert atmosphere, to the amino acid solution at 0° C. The reaction mixture is left under stirring at this temperature for 30 min. After this time, the solvent is evaporated and the white solid obtained is dissolved in 5 mL of DMF. The solution is added to the resin with 0.1 equivalent of DMAP (12.2 mg, 0.1 mmol) in 1 mL of DMF, and then the reaction mixture is left under stirring for 1 hour. The resin is then filtered, washed with 5 mL of DMF, 5 mL of dichloromethane and then dried under vacuum. The final charge of resin (0.95 mmol/g; 86%) is determined by UV quantification of the dibenzofulvene-piperidine adduct released during deprotection of aliquots with a 20% solution of piperidine in DMF.

Solid-phase synthesis of polypeptides is carried out using the Fmoc/tert-butyl strategy on Fmoc-Gly-Wang resin (scale of 0.5 mmol) prepared as previously on a microwave peptide synthesizer (CEM μ WAVES, Saclay, France). Coupling is carried out using a 5 times molar excess of each amino acid, the activator HBTU (O-benzotriazole-N,N,N',N'-tetramethyluronium hexafluorophosphate) is used with a 4.5 times molar excess and the base DiEA (diisopropylethylamine) is used with a 10 times molar excess. The final deprotection and cleavage of the polypeptide from the resin are carried out with 30 mL of a TFA (trifluoroacetic acid)/TIS (triisopropylsilane)/H$_2$O mixture (95/2.5/2.5 by volume) for 1 hour. The polypeptide is then obtained by precipitation in a diethyl ether/heptane mixture (1/1 by volume), dissolved in H$_2$O and then lyophilized. The purity of the polypeptide (79%) is determined by HPLC (liquid chromatography) and capillary electrophoresis. LC-MS analysis of the principal polypeptide is in agreement with the structure of the expected polypeptide (C$_{33}$H$_{43}$N$_9$O$_{10}$ calculated 726.32 Da [M+H]$^+$, observed 726.50 Da).

Example 3

Liquid-phase Synthesis of Polypeptide 1a (H-GF-GQGFGG-N(CH$_2$CH$_2$SH)$_2$)(SEQ ID NO: 1)

102 mg of polypeptide H-GFGQGFGG-OH (SEQ ID NO: 8) (0.14 mmol) is dissolved in a minimum amount of anhydrous dimethylformamide (DMF), and 39 μL of triethylamine (TEA) (2 equivalents, 0.28 mmol) is added to the solution. With stirring, 42 μL of di-tert-butyl dicarbonate (Boc$_2$O) (1.3 equivalent, 0.18 mmol) is added to the reaction mixture and the solution is homogenized by adding anhydrous DMF. The reaction is monitored by HPLC.

174.2 mg of bis({2-[triphenylmethyl)sulphanyl]ethyl}) amine (2 equivalents, 0.28 mmol) is added to the preceding reaction mixture. 32 μL of DiEA (1.3 equivalent, 0.18 mmol) and 94.7 mg of benzotriazol-1-yl-oxytripyrrolidinophosphonium hexafluorophosphate (PyBOP) (1.3 equivalent, 0.18 mmol) are added to the reaction mixture. Coupling is monitored by HPLC. The polypeptide resulting from this coupling step is then precipitated and washed in a large volume of cold diethyl ether. The polypeptide is then dissolved in a minimum amount of DMF, then precipitated and washed a second time in diethyl ether.

12.2 mL of a TFA/TIS/water mixture (95/2.5/2.5) is added to the protected polypeptide. The solution turns yellow immediately and quickly fades. After 30 min, the polypeptide is precipitated in 300 mL of a cold diethyl ether/heptane mixture (1/1). The solution is centrifuged and then the polypeptide is washed twice with the above mixture. The polypeptide is solubilized in water, frozen and then lyophilized. The product is then purified by preparative HPLC (gradient: 0 to 40% of buffer B in 40 min, flow rate: 6 mL/min). 60 mg of purified polypeptide is then obtained after lyophilization (total yield=50%).

The analysis of the product is as follows.

$^1$H NMR (500 MHz, DMF-d7).

Phe$_2$ (2.98, dd, 1H, Hβ; 3.23, dd, 1H, Hβ; 4.63, m, 1H, Hα; 7.19-7.33, m, 5H, H$_{arom}$); Gln$_4$ (1.98-2.15, m, 2H, Hβ; 2.31, m, 2H, Hγ; 4.37, dt, 1H, Hα; 6.97, s, 1H, NH$_2$; 7.57, s, 1H, NH$_2$; 8.09, d, 1H, NH); Phe$_6$ (2.98, dd, 1H, Hβ; 3.23, dd, 1H, Hβ; 4.63, m, 1H, Hα); Gly$_{1, 3, 5, 7, 8}$ (3.72-4.21, m, 10H, Hα; 8.6, broad s, 3H, NH$_3^+$ term.).

Bis(tritylmercaptoethyl)amino group: 2.22 (t, 1H, SH); 2.42 (t, 1H, SH); 2.68 (q, 2H, CH$_2$); 2.81 (q, 2H, CH$_2$); 3.5 (t, 2H, CH$_2$); 3.58 (t, 2H, CH$_2$).

$^{13}$C NMR (125 MHz, DMF-d7): Phe$_2$ (39.7, Cβ; 57.5, Cα; C$_{arom}$; CO); Gln$_4$ (30.2, Cβ; 34.1, Cγ; 55.9, Cα; CO); Phe$_6$ (39.7, Cβ; 58.2, Cα; C$_{arom}$; CO); Gly$_{1,3,5,7,8}$ (Cα; CO).

Bis(tritylmercaptoethyl)amino group: 24.0; 25.0; 52.0; 53.0.

Mass spectrometry: LC-MS C$_{37}$H$_{52}$N$_{10}$O$_9$S$_2$ [M+H]$^+$ calculated 845.34 Da; observed 845.42 Da.

Example 4

Deprotection of the Secondary amine bis({2-[triphenylmethyl)sulphanyl]ethyl})amine 12.5 mL of a TFA/TIS mixture (97.5/2.5) is poured onto 77.75 mg of bis({2-[triphenylmethyl)sulphanyl]ethyl})amine (0.125 mmol). The reaction mixture is left under stirring for 30 minutes. The solution is then evaporated to dryness in a rotary evaporator, obtaining a white solid. The solid obtained (compound of formula (VIII')) is solubilized in cyclohexane and evaporated to dryness; the operation is repeated twice.

Example 5

Coupling of the Deprotected Amine to the Chlorotrityl Resin 893 mg of resin (trityl chloride resin on skeleton of styrene copolymer with 1% of divinylbenzene, 200-400 mesh, 1.4 mmol/g, marketed by Merck under the reference 01-64-0074) is put in a reactor (1.25 mmol). Under argon, the amine from Example 4 is solubilized in 5 mL of anhydrous DMF and deposited on the resin using a gas-tight syringe. The reactor is stirred overnight under aluminium foil. 40.5 µL of methanol (1 mmol) and 116.5 µL of lutidine (1 mmol) are added to the resin. After solvolysis for 30 minutes, the resin is washed with 2×2 minutes of DMF, 2×2 minutes MeOH, 2×2 minutes DMF, 2×2 minutes 5% DIEA in DMF and finally 2×2 minutes DMF. Chloranil and Ellman colorimetric tests reveal the presence of a secondary amine and absence of free thiol on the resin.

The method for obtaining the functionalized resin of Example 5 corresponds to the following general diagram:

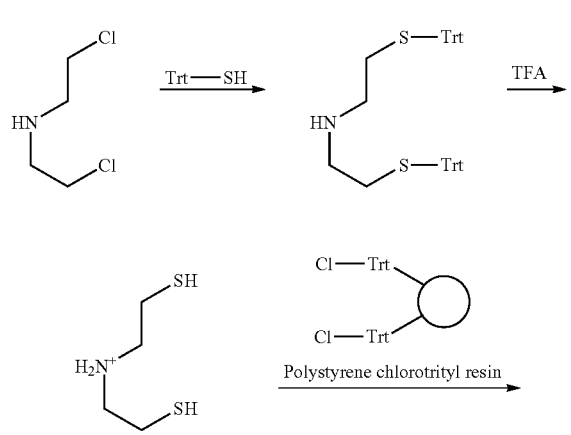

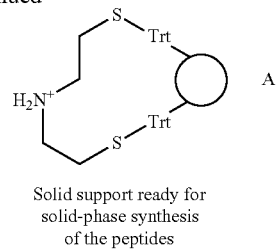

Solid support ready for solid-phase synthesis of the peptides

Example 6

Coupling of Amino Acids on the Functionalized Resin from Example 5 to Supply Primer Supports (Functionalized Resin Bearing a First Amino Acid)

0.5 mmol of Fmoc-AA-F (amino acid protected by an Fmoc group and activated in the form of an acid fluoride) is solubilized in 2 mL of anhydrous DCM and added to the resin from Example 5 (0.125 mmol). Then 82.4 µL of N-methylmorpholine (0.75 mmol) is added. The reaction is stirred at ambient temperature for 2 hours. The resin is then washed for 5×2 minutes with anhydrous DCM and 3×2 minutes DMF. Chloranil and Ellman colorimetric tests show absence of secondary amine and of free thiol on the resin.

The final charge of the resin is determined by UV-VIS assay at 290 nm of the dibenzofulvene-piperidine adduct released during deprotection with a 20% solution of piperidine in DMF.

This example is implemented with 4 different amino acids: glycine, alanine, valine and tyrosine.

A charge of 0.15 mmol/g is obtained for glycine; 0.124 mmol/g for alanine; 0.115 mmol/g for valine; and 0.107 mmol/g for tyrosine.

It should be noted that for coupling the first amino acid to the solid support, other coupling agents can be used such as PyBOP, PyBrop, HBTU etc. It was found that PyBrop gives the best results and allows direct use of the amino acids without the need for preactivation using an acid fluoride (which is less practical experimentally).

Example 7

Solid-phase Synthesis of the Polypeptides 1c (H-ILKEPVHGG-N(CH$_2$CH$_2$SH)$_2$), 1d (H-ILKEPVHGA-N(CH$_2$CH$_2$SH)$_2$), 1e (H-ILKEPVHGV-N(CH$_2$CH$_2$SH)$_2$) and 1f (H-ILKEPVHGY-N(CH$_2$CH$_2$SH)$_2$)

Polypeptide 1c (SEQ ID NO: 2) is obtained from the primer support prepared in Example 6 with glycine.

Polypeptide 1d (SEQ ID NO: 3) is obtained from the primer support prepared in Example 6 with alanine.

Polypeptide 1e (SEQ ID NO: 4) is obtained from the primer support prepared in Example 6 with valine.

Polypeptide 1f (SEQ ID NO: 5) is obtained from the primer support prepared in Example 6 with tyrosine.

The synthesis of the polypeptides can be summarized as follows:

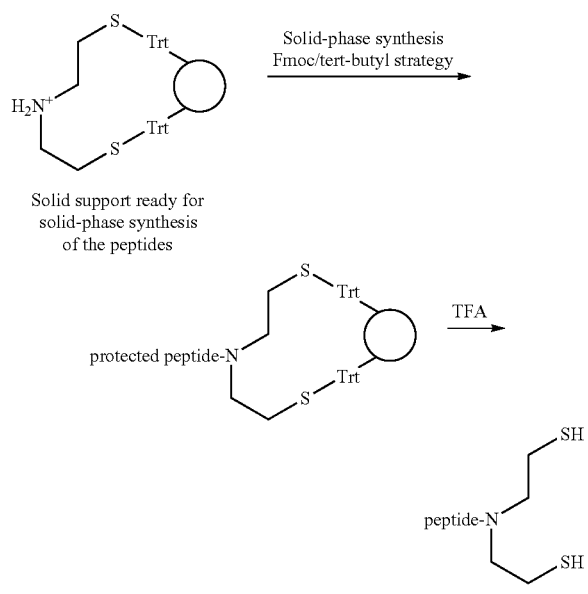

The polypeptides obtained in Example 7 have the following general formula:

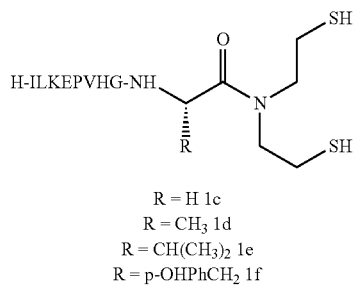

R = H 1c
R = CH₃ 1d
R = CH(CH₃)₂ 1e
R = p-OHPhCH₂ 1f

The solid-phase synthesis of the various polypeptides is carried out using the Fmoc/tert-butyl strategy on the respective resins from Example 6 (scale of 0.1 mmol) on a microwave peptide synthesizer (CEM μ WAVES, Saclay, France). Coupling is carried out using a 5 times molar excess of each amino acid, the activator HBTU is used with a 4.5 times molar excess and the base DiEA is used with a 10 times molar excess.

The final deprotection and cleavage of the polypeptide from the resin are carried out with 10 mL of a TFA/TIS/DMS/H$_2$O mixture (92.5/2.5/2.5/2.5 by volume) for 1 hour. The polypeptide is then obtained by precipitation in 100 mL of a diethyl ether/heptane mixture (1/1 by volume), dissolved in H$_2$O and then lyophilized.

The purity of each polypeptide is determined by HPLC (91% for polypeptide 1c with a glycine, 83% for polypeptide 1d, 80% for 1e, and 88% for 1f). MALDI-TOF analysis of the polypeptides is in agreement with the structure of the expected polypeptide (Peptide 1c $C_{47}H_{81}N_{13}O_{11}S_2$ [M+H]$^+$ calculated 1068.6 Da, observed 1068.5. Polypeptide 1d $C_{48}H_{83}N_{13}O_{11}S_2$ [M+H]$^+$ calculated 1082.6 Da, observed 1082.4. Polypeptide 1e $C_{50}H_{87}N_{13}O_{11}S_2$ [M+H]$^+$ calculated 1110.6 Da, observed 1110.5). Polypeptide 1f $C_{54}H_{87}N_{13}O_{12}S_2$ [M+H]$^+$ calculated 1174.6 Da, observed 1174.6).

The polypeptides are purified on a Nucleosil C18 column in acetonitrile-H$_2$O (80-20) in TFA, with a gradient from 0 to 30% in 30 min for polypeptide 1c, and a gradient from 0 to 10% in 5 min and then 10 to 25% in 25 min for polypeptides 1d and 1e.

The purity determined by HPLC is 96% for polypeptide 1c with an overall yield of 35%, 97% for polypeptide 1d with a yield of 31%, and 99% for polypeptide 1e with a yield of 27%.

Example 8

Ligation of Polypeptides 1c, 1d and 1f with Polypeptide 2 (H-CILKEPVHGV-NH$_2$)

The respective ligations of polypeptides 1c, 1d and 1f obtained in Example 7 with polypeptide 2 (SEQ ID NO: 6) are carried out according to the following diagram:

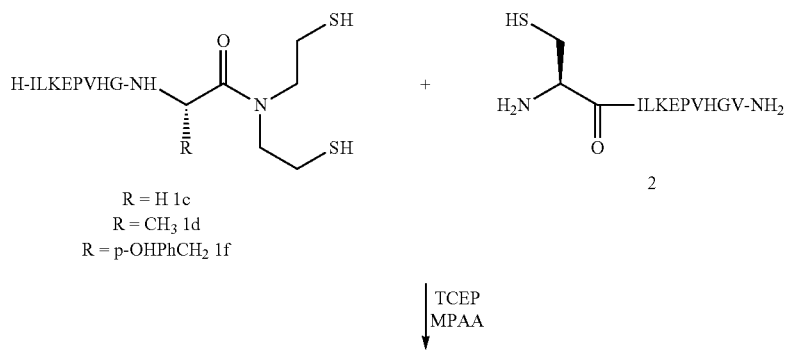

-continued

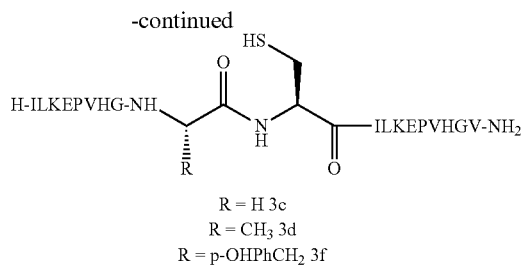

R = H 3c
R = CH₃ 3d
R = p-OHPhCH₂ 3f

These ligations make it possible to obtain the respective polypeptides 3c (of formula H-ILKEPVHG-GCILKEPVHGV-NH₂, SEQ ID NO: 9), 3d (of formula H-ILKEPVHGACILKEPVHGV-NH₂, SEQ ID NO: 10) and 3f (of formula H-ILKEPVHGYCILKEPVHGV-NH₂, SEQ ID NO: 11).

Ligation of polypeptide 1c.

336 mg of MPAA (2 mmol, 200 mM) and 234 mg of TCEP (800 μmol, 80 mM) are dissolved in 10 mL of 0.1 M phosphate buffer (pH adjusted to 7.5). 10.2 mg of polypeptide 1c is dissolved in the mixture (7.2 μmol, 0.72 mM), this solution is added to 15.3 mg of polypeptide 2 H-CILKEPVHGV-NH₂ (10.6 mmol, 1.06 mM). The mixture is placed under argon and then stirred at 37° C. The product is then purified by RP-HPLC to give 5.9 mg of polypeptide 3c (32%).

Ligation of polypeptide 1d.

First, an MPAA/TCEP.HCl solution is prepared. 33.52 mg of MPAA and 57.54 mg of TCEP.HCl are weighed in a 1.5-mL polypropylene tube. 1 mL of 0.1M phosphate buffer at pH=7.3 and then 140 μL of 6M NaOH are added, leading to complete solubilization of the powders. An additional 20 μL of 6M NaOH is added to adjust the solution pH to 7.05.

For the actual ligation reaction, 5.99 mg of polypeptide 1d and 9.05 mg of polypeptide 2 are weighed in the same 5-mL glass flask. 600 μL of the above solution is added. The reaction mixture is put under argon in 3 vacuum/argon cycles, then placed in an oil bath thermostatically controlled to 37° C. and stirred using a magnetic bar.

After 26.5 h, the reaction mixture is transferred to a 15-mL polypropylene tube. The reaction flask is rinsed with 3.4 mL of buffer A (water containing 0.05 vol. % of TFA), which is transferred to the 15-mL tube. 4 extractions (4×4 mL) are carried out with ether. The aqueous phase is acidified further by adding 150 μL of TFA at 10% in water. 4 new extractions (4×4 mL) with ether are repeated.

The aqueous phase is then injected in preparative HPLC (ambient temperature, 230 nm, Nucleosil C18 column 120 A-5 μm, buffer A (water containing 0.05 vol. % of TFA), buffer B acetonitrile/water 4/1 by volume containing 0.05 vol. % of TFA, flow rate 3 mL/min, gradient 0 to 15% B in 15 min, then 15 to 100% B in 283 min, volume injected 4 mL).

After lyophilization, 8.5 mg of ligation product is collected (yield=77%).

$C_{93}H_{156}N_{26}O_{23}S$ [M+H]⁺ calculated 2038.16. Found 2038.07.

Determination of enantiomeric purity for alanine: 1.76% D-enantiomer.

Ligation of polypeptide 1f.

First, an MPAA/TCEP.HCl solution is prepared. 33.63 mg MPAA and 57.37 mg of TCEP.HCl are weighed in a 1.5-mL polypropylene tube. 1 mL of 0.1 M phosphate buffer pH=7.3 and then 140 μL of 6M NaOH are added, leading to complete dissolution of the powders. The solution pH is adjusted to 7.05 with 6M NaOH.

For the ligation reaction proper, 3.97 mg of polypeptide 1e and 5.75 mg of polypeptide 2 are weighed in the same 5-mL glass flask. 374 μL of the above solution is added. The reaction mixture is put under argon in 3 vacuum/argon cycles, then placed in an oil bath thermostatically controlled to 37° C. and stirred using a magnetized bar.

After 44.5 h, 78.6 μL (30 eq) of a 1M solution of TCEP.HCl in phosphate buffer adjusted to pH=7.0 with 6N soda is added.

After 4.5 days, the reaction mixture is transferred to a 15-mL polypropylene tube. The reaction flask is rinsed with 3.5 mL of buffer A and acidified with 150 μL of TFA at 10% in water, which is also transferred to the tube. 3 extractions (3×5.5 mL) are carried out with ether.

The aqueous phase is then injected in preparative HPLC (ambient temperature, 230 nm, Nucleosil C18 column 120 A-5 μm, buffer A 100% water containing 0.05% TFA, buffer B acetonitrile/water 4/1 containing 0.05% TFA, flow rate 3 ml/min, gradient 0 to 15% B in 15 min, then 15 to 100% B in 283 min, volume injected 4 mL).

After lyophilization, 3.80 mg of ligation product is collected (yield=54%).

$C_{99}H_{160}N_{26}O_{24}S$ [M+H]⁺ calculated 2130.18. Found 2130.2.

Determination of enantiomeric purity of Tyr: 1.25% D-enantiomer.

Figure 2A:
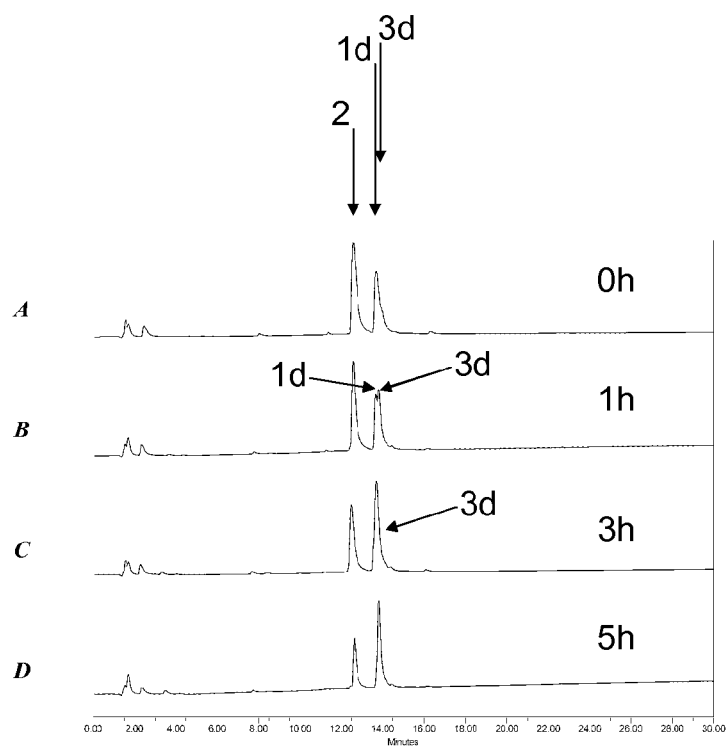
FIGS. 2a and 2b show the monitoring, by RP-HPLC (reverse-phase high-performance liquid chromatography), of native ligation between polypeptide 1d and polypeptide 2, to obtain polypeptide 3d, according to Example 7. Plot A corresponds to the time point t=0; plot B corresponds to the time point t=1 h; plot C corresponds to the time point t=3 h; plot D corresponds to the time point t=5 h; and plot E corresponds to the time point t=22 h.
Figure 2B:
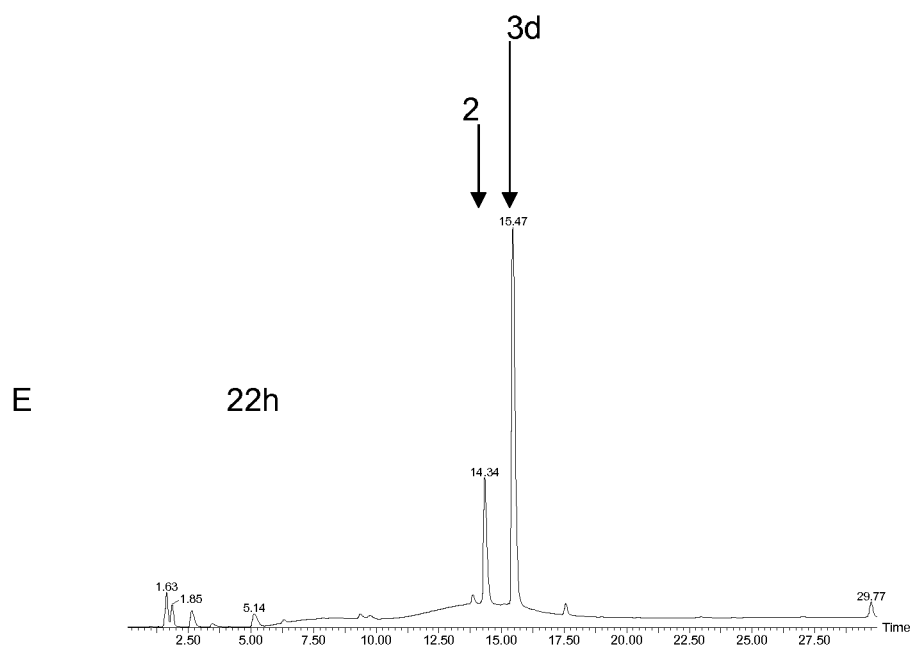
Figure 2C:
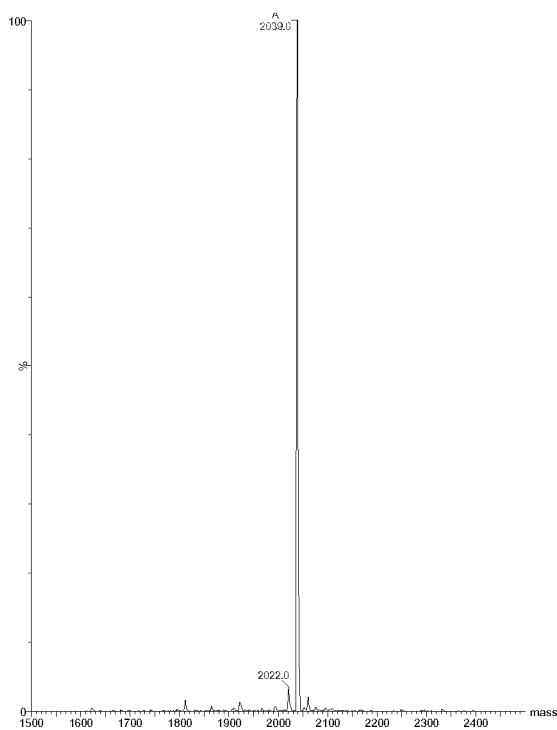
FIG. 2c shows the deconvoluted mass spectrometry spectrum for the peak of polypeptide 3d obtained at the time point t=22 h (FIG. 2b).
Figure 3A:
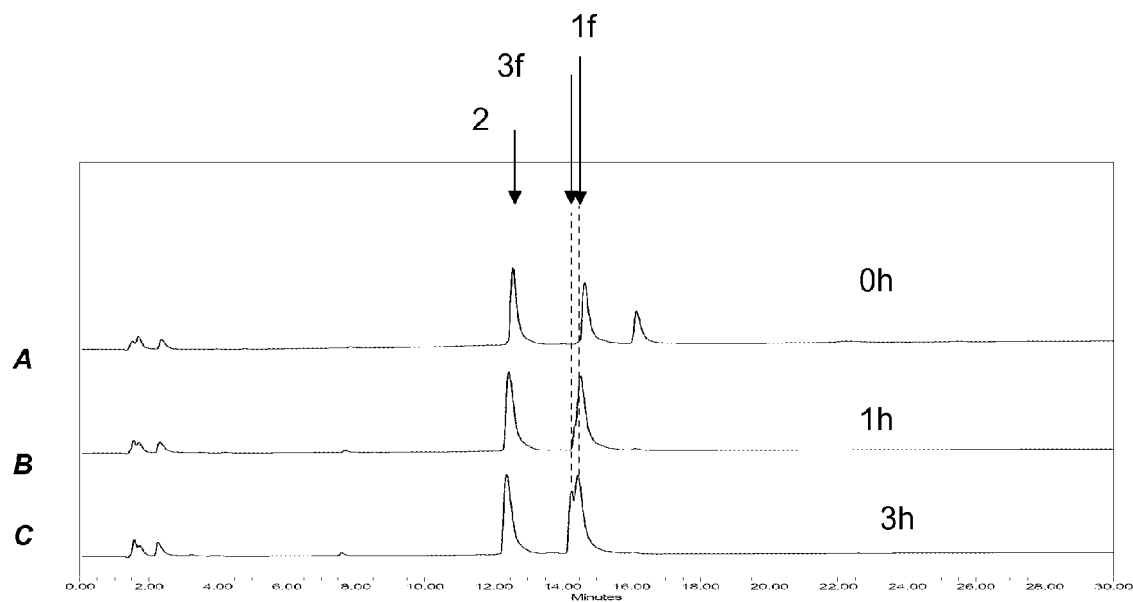
FIGS. 3a to 3c show the monitoring, by RP-HPLC (reverse-phase high-performance liquid chromatography), of native ligation between polypeptide 1f and polypeptide 2, to obtain polypeptide 3f, according to Example 7. Plot A corresponds to the time point t=0; plot B corresponds to the time point t=1 h; plot C corresponds to the time point t=3 h; plot D corresponds to the time point t=6 h; and plot E corresponds to the time point t=27 h.
Figure 3B:
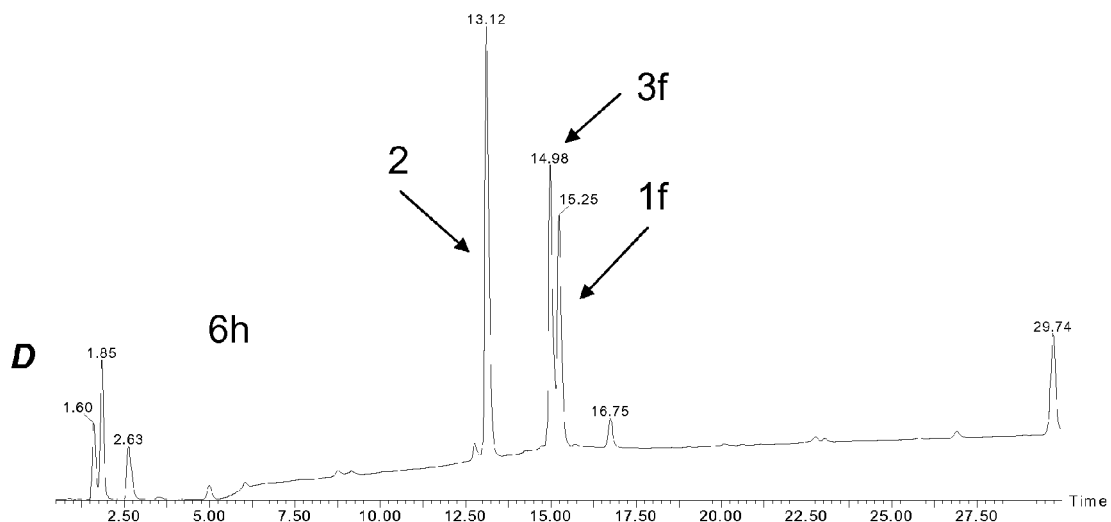
Figure 3C:
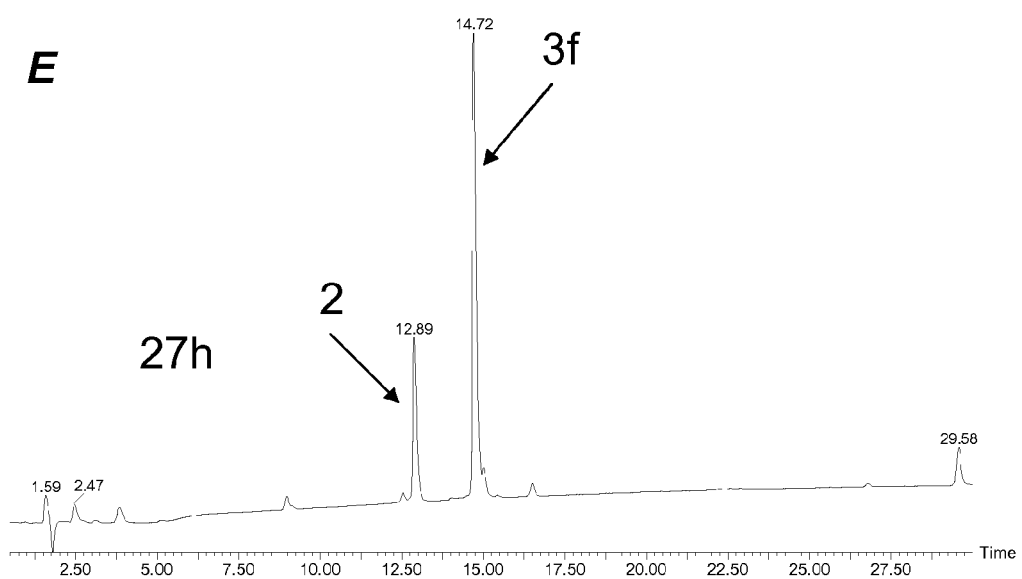
Figure 3D:
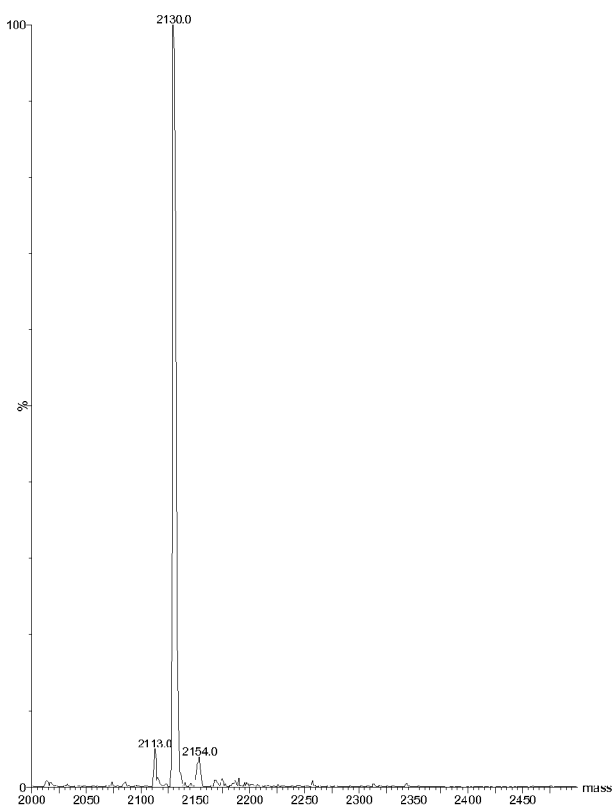
FIG. 3d shows the deconvoluted mass spectrometry spectrum for the peak of polypeptide 3f obtained at the time point t=27h (FIG. 3c).

FIGS. 1 to 3d illustrate the monitoring of the ligation reaction for the ligation of polypeptides 1c, 1d and 1f.

Example 9

Solid-phase Synthesis of Polypeptide 1g (H-CHHLEPGG-N(CH₂CH₂SH₂) and Cyclization of this Polypeptide Polypeptide 1g (SEQ ID NO: 7) was synthesized as with polypeptide 1c.

The solid-phase synthesis of polypeptide 1g is carried out using the Fmoc/tert-butyl strategy (scale 50 μmol) on a microwave peptide synthesizer. Coupling is carried out in the presence of HTBU as activating agent (4.5 eq) and DIEA as base (10 eq). At the end of synthesis, the resin is washed with dichloromethane (2×5 mL), with ethyl ether (2×5 mL), and then dried. The final deprotection and cleavage of the polypeptide are carried out with 5 mL of TFA/TIS/H₂O/DMS mixture, 9.25/0.25/0.25/0.25 by volume for one hour. The polypeptide is precipitated in 50 mL of an ether/heptane mixture (1/1), dissolved in water and then lyophilized.

Polypeptide 1g: $C_{39}H_{61}N_{13}O_{10}S_3$, MALDI-TOF analysis [M+H]⁺ calculated 968.19, observed 968.2.

Polypeptide 1g is then cyclized to provide polypeptide 3g, according to the following diagram:

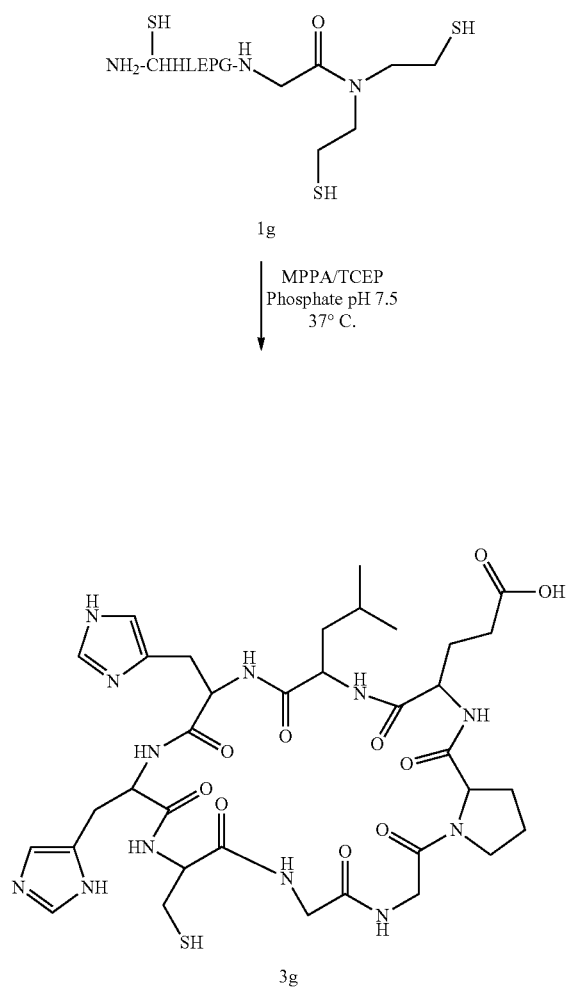

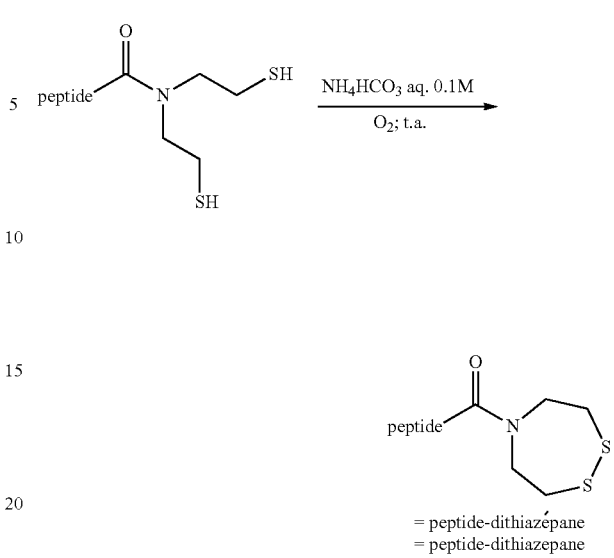

= peptide-dithiazépane
= peptide-dithiazepane

Each polypeptide is cleaved from the solid support by the action of TFA/DMS/TiS/H$_2$O solution (92.5/2.5/2.5/2.5; v/v). The polypeptide is then precipitated in a large volume of a diethyl ether/heptane mixture (1/1; v/v) and washed twice using this solution. The crude polypeptide lyophilized after the cleavage step is then dissolved in a 0.1M solution of ammonium bicarbonate previously degassed for 10 min by bubbling with nitrogen (1 mg/mL).

The mixture is then stirred vigorously at ambient temperature. The development of the reaction is monitored by MALDI-TOF mass spectrometry until the reduced form of the polypeptide in question has disappeared completely. The polypeptide is finally purified by RP-HPLC (gradient eluent A (H$_2$O/0.05% TFA)/eluent B (80% acetonitrile/20% H$_2$O/ 0.05% TFA): 0 to 10% in 10 min then 10% to 25% in 25 min), then frozen and lyophilized.

The following table summarizes the results obtained (MALDI-TOF analysis).

The conditions used for cyclization are identical to the conditions used for ligation of polypeptide 1c to polypeptide 2.

33.64 mg of MPAA (200 mM) and 22.9 mg of TCEP (80 mM) are dissolved in 1 mL of 0.1 M phosphate buffer at pH 7.5 adjusted with 6N NaOH solution.

1.0 mg (0.76 µmol) of polypeptide 1g is dissolved in the mixture (764 µL, 1 mM), placed under argon and then stirred at 37° C. The reaction leads exclusively to formation of the cyclic polypeptide 3g (SEQ ID NO: 12).

Polypeptide 3g: cyclo(CHHLEPGG); C$_{35}$H$_{49}$N$_{12}$O$_{10}$S MALDI-TOF analysis [M+H]+ calculated 831.1 observed 831.1.

| Polypeptide | m/z [M + H]$^+_{calc.}$ | m/z [M + H]$^+_{obs.}$ | Final yield (%) |
|---|---|---|---|
| 1c | 1066.6 | 1066.6 | 17 |
| 1d | 1080.6 | 1080.6 | 13 |
| 1e | 1108.6 | 1108.6 | 23 |
| 1f | 1172.6 | 1172.6 | 20 |

Example 10

Oxidation of Polypeptides 1c, 1d, 1e and 1f to Dithiazepanes (SEQ ID NO: 13, 14, 15 and 16)

Polypeptides 1c, 1d, 1e and 1f are as obtained in Example 7. These polypeptides are oxidized according to the following general diagram:

Example 11

Ligation Between Polypeptide 1c and Polypeptide 4

Polypeptide 1c (SEQ ID NO: 2) is ligated to polypeptide 4 (SEQ ID NO: 17), which is identical to polypeptide 2 except that the N-terminal cysteine is replaced with a homocysteine. This reaction makes it possible to obtain polypeptide 5 (SEQ ID NO: 18). The reaction diagram is as follows:

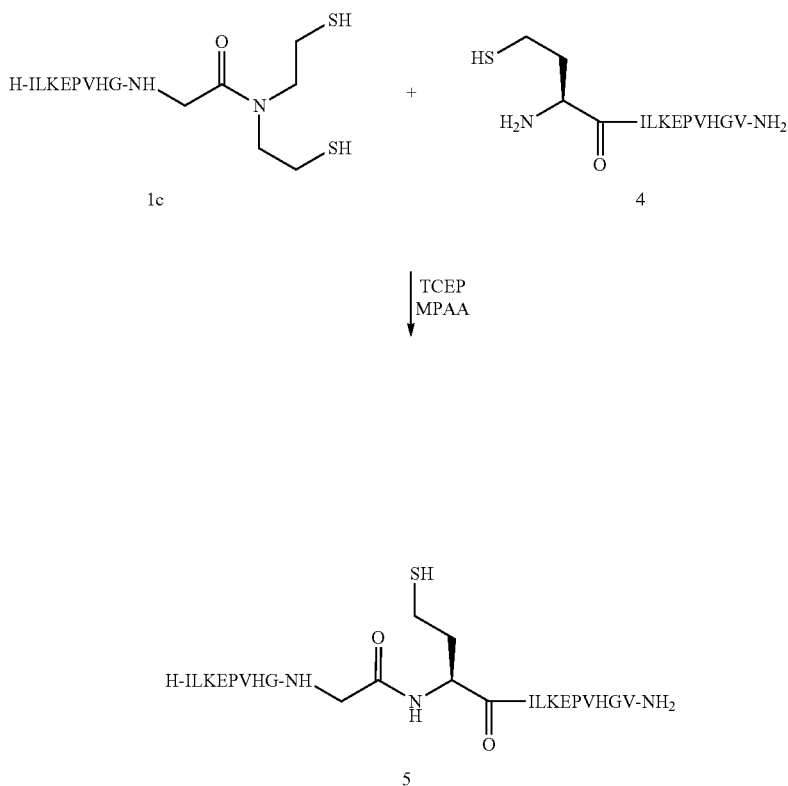

33.6 mg of MPAA (0.2 mmol, 200 mM) and 57.4 mg of TCEP (0.2 mmol, 200 mM) are dissolved in 1 mL of 0.1 M phosphate buffer (pH adjusted to 7.35). 6.15 mg of polypeptide 1c (4.4 μmol, 7 mM) and 9.35 mg of polypeptide 4 (H-homoCysILKEPVHGV-NH$_2$) (6.55 μmol, 10.5 mM) are dissolved in the mixture (624 μL). The mixture is placed under argon and then stirred at 37° C. The product is then purified by RP-HPLC to give 3.3 mg of polypeptide 5 (29%). C$_{91}$H$_{152}$N$_{26}$O$_{23}$S. MALDI-TOF MS analysis (monoisotopic) [M+H]$^+$ 2010.12 calculated, 2009.5 found.

Example 12

Synthesis of Polypeptide 6 (SEQ ID NO: 19)

Polypeptide 6 Has The Following Sequence:

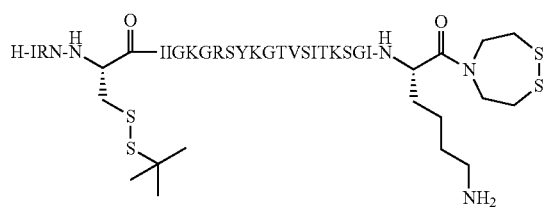

The resin described in Example 5 (0.5 mmol, 0.175 mmol/g) is conditioned in dichloromethane. Fmoc-Lys(Boc)-OH (2.342 g, 5 mmol) is dissolved in dichloromethane and a few drops of DMF to aid solubilization, and then added to the resin. PyBrop (2.331 g, 5 mmol) is dissolved in a minimum amount of dichloromethane and then added to the resin. DIEA (2.613 mL, 15 mmol) is then added to the resin and coupling takes 2 h. The resin is then washed for 3×2 minutes with dichloromethane. The resin is then treated with 10% Ac$_2$O/5% DiEA/dichloromethane (10 mL, 2 min) then (10 mL, 20 min). The resin is then washed for 5×2 minutes with dichloromethane.

Polypeptide 6 is assembled on a portion of the preceding resin (0.25 mmol, 0.175 mmol/g) with a peptide synthesizer (CEM μWaves, Saclay, France), using the Fmoc/tert-butyl strategy. Coupling is carried out with the amino acids (0.2 M, 4 eq), the activator HBTU (0.5 M, 3.6 eq) and the base DIEA (2 M, 8 eq). The final deprotection and cleavage of the peptide from the resin are carried out with TFA/TIS/DMS/thioanisole/H$_2$O (90/2.5/2.5/2.5/2.5 by volume, 25 mL) for 2.5 h. The peptide is precipitated in cold diethyl ether/heptane mixture (1/1 by volume), dissolved in a minimum amount of water and lyophilized. 288 mg of crude peptide is obtained (yield=32%). C$_{120}$H$_{216}$N$_{36}$O$_{31}$S$_4$ LC-MS [M+H]$^+$ calculated (average mass) 2788.5; observed 2788.1.

A portion of polypeptide 6 is then oxidized before purification. For this, polypeptide 6 (49.8 mg) is dissolved in AcOH/water 4/1 (2 mL). It is added dropwise to a solution of iodine in AcOH/water 4/1 (25 mL, "10 eq"). After stirring for 10 minutes, the reaction mixture is transferred to a separating funnel containing water (60 mL). 3 extractions with ether are carried out (3×60 mL). The aqueous phase is frozen and lyophilized to give 44.1 mg of crude peptide.

After purification by RP-HPLC (column: Atlantis dC18 OBD 5 μm, 19×100 mm, 210-300 nm, buffer A 100% water containing 0.05% TFA, buffer B CH$_3$CN/water 4/1 containing 0.05% TFA, gradient: 20 to 40% of buffer B in 40 min, flow rate 25 mL/min), 7.2 mg of pure peptide is obtained (yield=14.5%) C$_{120}$H$_{214}$N$_{36}$O$_{31}$S$_4$ LC-MS [M+H]$^+$ calculated (average mass) 2786.52; observed 2786.33.

Example 13

Synthesis of Polypeptide 7 (SEQ ID NO: 20)

Polypeptide 7 has the following sequence:

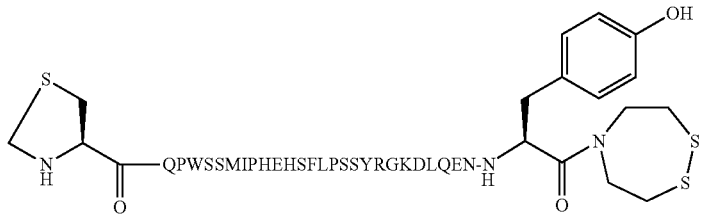

The resin described in Example 5 (0.5 mmol, 0.175 mmol/g) is conditioned in dichloromethane. Fmoc-Tyr-OH (2.298 g, 5 mmol) is dissolved in dichloromethane (<5 mL) and a few drops of DMF to aid solubilization, then added to the resin. PyBrop (2.331 g, 5 mmol) is dissolved in a minimum amount of DCM and then added to the resin. DIEA (2.614 mL, 15 mmol) is then added to the resin and coupling takes 2 h. The resin is then washed for 4×2 minutes with dichloromethane. The resin is then treated with 10% $Ac_2O$/5% DiEA/DCM (10 mL, 2 min) then (10 mL, 20 min). The resin is then washed for 5×2 minutes with dichloromethane.

Polypeptide 7 is assembled on the preceding resin (0.5 mmol, 0.175 mmol/g) with a peptide synthesizer (CEM µWaves, Saclay, France), using the Fmoc/tert-butyl strategy. Coupling is carried out with the amino acids (0.2 M, 4 eq), the activator HBTU (0.5 M, 3.6 eq) and the base DIEA (2 M, 8 eq). The washing solvent (DMF) and the solvent of Fmoc-Met-OH contain 1% of thioanisole for maximum avoidance of oxidation of the methionine of the sequence.

The resin is separated into 2 after the glutamine in position 2 (0.25 mmol) in order to couple the Boc-L-Thz-OH manually. To do this, the resin is washed for 4×2 minutes with DMF, weighed in DMF and divided into 2. HBTU (379.3 mg, 1 mmol) is dissolved in DMF (1100 µL). HOBt (135 mg, 1 mmol) is dissolved in DMF (500 µL) and added to the HBTU. Boc-L-Thz-OH (233.29 mg, 1 mmol) is dissolved in DMF (500 µL) and added to the HBTU/HOBt mixture. DIEA (522.7 µL, 3 mmol) is then added to the mixture. It is stirred for 1 minute, then the mixture is added to the resin and coupling takes 45 minutes. The resin is then washed for 4×2 minutes with DMF, 4×2 minutes with dichloromethane and then 3×2 minutes with $Et_2O$ and dried.

The final deprotection and cleavage of the peptide from the resin are carried out with TFA/TIS/DMS/thioanisole/$H_2O$ (90/2.5/2.5/2.5/2.5 by volume, 25 mL) for 2.5 h. The peptide is precipitated in a cold diethyl ether/heptane mixture (1/1 by volume), dissolved in a minimum amount of water and lyophilized. 369 mg of crude peptide is obtained (yield=37.6%). $C_{153}H_{223}N_{41}O_{44}S_4$ MALDI-TOF $[M+H]^+$ calculated (monoisotopic resolution) 3467.54; observed 3466.0.

A portion of polypeptide 7 is then oxidized before purification. For this, fragment 2 (51.8 mg) is dissolved in $CH_3CN$ (2.38 mL) and then 0.2 M phosphate buffer pH=7.3 (9.50 mL) is added. It is added dropwise to a solution of 10 mM diamide in water (1.32 mL, 1 eq). After stirring for 15 minutes, the reaction mixture is diluted with buffer A (1.8 mL) and injected in RP-HPLC (column: Atlantis dC18 OBD 5 µm, 19×100 mm, 210-300 nm, buffer A 100% water containing 0.05% TFA, buffer B $CH_3CN$/water 4/1 containing 0.05% TFA, gradient: 25 to 45% of buffer B in 40 min, flow rate 25 mL/min); 11.2 mg of pure peptide is obtained (yield=21.6%) $C_{153}H_{221}N_{41}O_{44}S_4$ LC-MS $[M+H]^+$ calculated (average mass) 3467.97; 3467.38.

Example 14

Synthesis of Polypeptide 8 (SEQ ID NO: 21)

Polypeptide 8 has the following sequence:

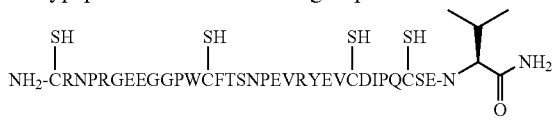

Polypeptide 8 is assembled on Novasyn TGR resin (0.5 mmol, 0.25 mmol/g) with a peptide synthesizer (CEM µWaves, Saclay, France), using the Fmoc/tert-butyl strategy. Coupling is carried out with the amino acids (0.2 M, 4 eq), the activator HBTU (0.5 M, 3.6 eq) and the base DIEA (2 M, 8 eq). The final deprotection and cleavage of the peptide from the resin are carried out with TFA/EDT/$H_2O$/TIS (94/2.5/2.5/1 by volume, 30 mL) for 2.5 h. The peptide is precipitated in a cold diethyl ether/heptane mixture (1/1 by volume), dissolved in a minimum amount of water and lyophilized. After RP-HPLC purification (Vydac C18 column 50 cm×2 cm, 280 nm, buffer A 100% water containing 0.05% TFA, buffer B $CH_3CN$/water 4/1 containing 0.05% TFA, gradient: 0 to 20% of buffer B in 10 min then 20 to 50% of buffer B in 60 min, flow rate 30 mL/min), 272 mg of pure peptide is obtained (yield=13%) $C_{158}H_{239}N_{47}O_{52}S_4$ MALDI-TOF $[M+H]^+$ calculated (monoisotopic resolution) 3755.6; observed 3755.7.

Example 15

Ligation of Polypeptide 7 and of Polypeptide 8 (In Glove Box) to Obtain Polypeptide 7-8 (SEQ ID NO: 22)

MPAA (33.70 mg) and TCEP.HCl (57.30 mg) are dissolved in 0.1 M phosphate buffer pH=7.3 containing 4 M guanidine HCl (1 mL). The solution pH is adjusted to 7.2 with 5N soda (200 µL). The polypeptides 7 (8.5 mg) and 8 (18.25 mg, 2 eq) are weighed in the same tube and dissolved with the previous solution (309 µL). The reaction mixture is placed in a bath at 37° C. After 24 h, the reaction mixture is diluted with the same solution (300 µL).

25 h later, 56 mM O-methylhydroxylamine in 0.1 M acetate buffer at pH=3.93 (1.52 mL) is added. The pH of the reaction mixture is adjusted to pH=4.15 with acetic acid (35 µL). After 20 h at 37° C., the reaction mixture is taken out of the glove box. MPAA is extracted with $Et_2O$ (3×6 mL). The reaction mixture is treated for 20 minutes with TCEP.HCl (28 mg) before purification by RP-HPLC (Uptisphere 5C4 column 27.5 cm×1 cm, 215 nm, buffer A 100% water containing 0.05% TFA, buffer B $CH_3CN$/water 4/1 containing 0.05%

TFA, gradient: 0 to 20% of buffer B in 3 min then 20 to 50% of buffer B in 57 min, flow rate 6 mL/min). 4.4 mg of pure polypeptide 7-8 is obtained (yield=25.4%) $C_{306}H_{451}N_{87}O_{96}S_6$ MALDI-TOF [M+H]$^+$ calculated (average mass) 7077.8; observed 7078.5.

Example 16

Ligation of Polypeptide 6 and of Polypeptide 7-8 (In Glove Box) to Obtain Polypeptide 6-7-8 (SEQ ID NO: 23)

MPAA (33.74 mg) and TCEP.HCl (57.54 mg) are dissolved in 0.1 M of phosphate buffer at pH=7.3 containing 4 M of guanidine HCl (1 mL). The solution pH is adjusted to 7.2 with 5 N soda (220 µL). The polypeptides 7-8 (3.85 mg) and 6 (2.89 mg, 1.7 eq) are weighed in the same tube and dissolved with the aforementioned solution (115 µL). The reaction mixture is placed in a bath at 37° C.

After 24 h, formation of the ligation product is observed, namely polypeptide 6-7-8 of sequence: H-IRNCI-IGKGRSYKGTVSITKSG IKCQPWSSMIPHEHS-FLPSSYRGKDLQENYCRNPRGEEGGPWCFTSNPEV RYEVCDIPQCSEV-NH$_2$ $C_{418}H_{648}N_{122}O_{127}S_7$ MALDI-TOF [M+H]$^+$ calculated (average mass) 9640.01; observed 9640.1.

The invention claimed is:

1. Method for manufacturing a polypeptide of formula:

$$X_1-X''-X_2 \quad (III)$$

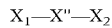

$X_1$ and $X_2$ each representing a peptide fragment, and $X''$ representing an amino acid residue comprising a thiol function, wherein said method comprises at least one step of ligation reaction between a polypeptide of formula:

$$X_1-N(CH_2CH_2SH)_2 \quad (I)$$

and a polypeptide of formula:

$$H-X''-X_2. \quad (II)$$

2. Method according to claim 1, in which the ligation reaction is carried out by bringing a polypeptide of formula:

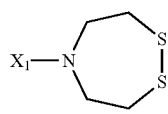

(I')

into contact with the polypeptide of formula (II), in the presence of at least one compound that reduces the disulphide bonds, the polypeptide of formula (I') being reduced in situ to the polypeptide of formula (I) for the ligation reaction.

3. Method according to claim 1, in which $X_2$ represents a peptide fragment of formula $$X_2'-(X_i''-X_i')_{i=3\ldots n} \quad (IV)$$

n being an integer greater than or equal to 3, each $X_i''$, for i an integer comprised between 3 and n, representing an amino acid residue bearing a thiol function, and each $X_i'$, for i an integer comprised between 2 and n, representing a peptide fragment;

said method comprising, before the step of ligation reaction between the polypeptide of formula (I) and the polypeptide of formula (II), a succession of n−2 steps of ligation reaction, the $j^{th}$ step of ligation reaction, for j an integer comprised between 1 and n−2, being a ligation reaction between a polypeptide of formula:

$$H-X_{i-j}''-X_{n-j}'-N(CH_2CH_2SH)_2 \quad (V)$$

in which the amine function and/or the thiol function of the residue $X_{n-j}''$ is protected and a polypeptide of formula:

$$H-(X_i''-X_i')_{i=(n-j+1)\ldots n} \quad (VI)$$

to form a polypeptide of formula:

$$H-(X_i''-X_i')_{i=(n-j)\ldots n} \quad (VII)$$

the polypeptide of formula (VII) undergoing deprotection of the thiol function of the residue $X_{n-j}''$ at the end of the ligation reaction.

4. Method according to claim 3, in which one or more of the n−2 steps of ligation reaction between the polypeptide of formula (V) and the polypeptide of formula (VI) is carried out by bringing a polypeptide of formula:

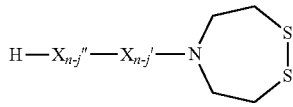

(V')

into contact with the polypeptide of formula:

$$H-(X_i''-X_i')_{i=(n-j+1)\ldots n} \quad (VI)$$

j being an integer comprised between 1 and n−2, in the presence of at least one compound that reduces the disulphide bonds.

5. Method according to claim 1 for manufacturing a cyclic polypeptide of formula:

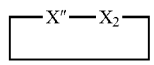

(X)

$X_2$ representing a peptide fragment, and $X''$ representing an amino acid residue comprising a thiol function, wherein said method comprises at least one step of ligation reaction of a polypeptide of formula:

$$H-X''-X_2-N(CH_2CH_2SH)_2 \quad (XI)$$

with itself.

6. Method according to claim 5, in which the ligation reaction is carried out by bringing a polypeptide of formula:

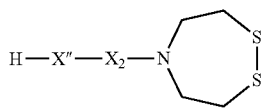

(XI')

into contact with at least one compound that reduces the disulphide bonds, the polypeptide of formula (XI') being reduced in situ to the polypeptide of formula (XI) for the ligation reaction.

7. Method according to claim 1, in which the ligation reaction is carried out in an aqueous medium at a pH between 6.5 and 8.5.

8. Method according to claim 1, in which the ligation reaction is carried out in the presence of at least one compound that reduces the disulphide bonds, selected from tris (2-carboxyethyl)phosphine, 4-mercaptophenylacetic acid, dithiothreitol, benzyl mercaptan and mixtures thereof.

9. Polypeptide of formula:

$$X_1-N(CH_2CH_2SH)_2 \quad (I)$$

or of formula:

$$X_1-N\underset{\underset{S}{|}}{\overset{S}{\diagup}}\phantom{xx}(I')$$

in which $X_1$ represents a peptide fragment and the group $$-N(CH_2CH_2SH)_2 \quad \text{or} \quad -N\underset{\underset{S}{|}}{\overset{S}{\diagup}}$$

is bound to the C=O termination of the amino acid residue of peptide fragment $X_1$ that is in C-terminal position.

10. Polypeptide according to claim 9, in which $X_1$ comprises between 2 and 300 amino acid residues.

11. Method according to claim 1, wherein the method further comprises manufacturing a polypeptide of formula:

$$X_1-N(CH_2CH_2SH)_2 \qquad (I)$$

comprising at least one step of peptide synthesis and one step of C-terminal functionalization, wherein the step of peptide synthesis precedes the step of functionalization; the step of peptide synthesis supplies a polypeptide of formula:

$$X_1-OH \qquad (IX)$$

comprising protective groups on its amine and carboxylic functions, with the exception of its C-terminal carboxylic function; and the step of functionalization comprises:
reaction of the polypeptide of formula (IX) with the amine compound of formula:

$$NH(CH_2-CH_2-S-G_1)_2 \qquad (VIII)$$

in which $G_1$ represents a protective group, said protective group in the liquid phase, to form the polypeptide of formula (I); and
optionally deprotection of the polypeptide of formula (I).

12. Polymer resin support for solid-phase synthesis of polypeptides, comprising a main skeleton and function groups selected from:
NH—($CH_2CH_2$—S-Trt-)$_2$ functional groups,
NH—($CH_2CH_2$—S-Trt-CO—NH—)$_2$ functional groups,
$G_2$AA-N—($CH_2CH_2$—S-Trt-)$_2$ functional groups, or
G2-AA-N—($CH_2CH_2$—S-Trt-CO—NH—)$_2$ functional groups,
where Trt represents a triphenylmethyl group or a substituted triphenylmethyl group in which the NH—($CH_2CH_2$—S-Trt-)$_2$ functional groups are bound to the main skeleton by the two triphenylmethyl groups, or the NH—($CH_2CH_2$—S-Trt-CO—NH—)$_2$ or $G_2$-AA-N ($CH_2CH_2$—S-Trt-)$_2$ functional groups are bound to the main skeleton by the two triphenylmethyl groups, or the NH—($CH_2CH_2$—S-Trt-CO—NH—)$_2$ functional groups or the $G_2$-AA-N—($CH_2CH_2$—S-Trt-CO—NH—)$_2$ functional groups are bound to the main skeleton by the two amine groups, and wherein $G_2$ is a hydrogen atom or a protective group of amine function.

13. Polymer resin support according to claim 12, in which the main skeleton is selected from the polystyrene, polyacrylamide, polyethylene glycol, cellulose, polyethylene, polyester, latex, polyamide, polydimethylacrylamide, polyethylene glycol-polystyrene copolymer, polyethylene glycol-polyacrylamide copolymer skeletons and derivatives thereof.

14. Method according to claim 1, wherein the method comprises manufacturing a polypeptide of formula:

$$X_1-N(CH_2CH_2SH)_2 \qquad (I)$$

said manufacturing comprising at least one step of peptide synthesis and one step of C-terminal functionalization, in which:
the step of functionalization precedes the step of peptide synthesis;
the step of functionalization comprises:
coupling an amino acid to a polymer resin support, to supply a primer support;
wherein the polymer resin support comprises a main skeleton and function groups selected from:
NH—($CH_2CH_2$—S-Trt-)$_2$ functional groups, or
NH—($CH_2CH_2$—S-Trt-CO—NH—)$_2$ functional groups,
where Trt represents a triphenylmethyl group or a substituted triphenylmethyl group in which the NH—($CH_2CH_2$—S-Trt-)$_2$ functional groups are bound to the main skeleton by the two triphenylmethyl groups, or the NH—($CH_2CH_2$—S-Trt-CO—NH—)$_2$ functional groups are bound to the main skeleton by the two triphenylmethyl groups, or by the two amine groups.

15. Method according to claim 2, wherein the method comprises a step of manufacturing a polypeptide of formula:

$$X_1-N\underset{\underset{S}{|}}{\overset{S}{\diagup}}\phantom{xx}(I')$$

in which $X_1$ represents a peptide fragment and the $$-N\underset{\underset{S}{|}}{\overset{S}{\diagup}}$$

group is bound to the C=O termination of the amino acid residue of peptide fragment $X_1$ that is in C-terminal position, comprising a step of oxidation of a polypeptide of formula:

$$X_1-N(CH_2CH_2SH)_2 \qquad (I)$$

in contact with the air, or in the presence of $I_2$ or of diamide, and in a buffer.

16. Method according to claim 1, wherein the method comprises manufacturing a polypeptide of formula:

$$X_1-N(CH_2CH_2SH)_2 \qquad (I)$$

said manufacturing comprising at least one step of peptide synthesis and one step of C-terminal functionalization, in which:
the step of functionalization precedes the step of peptide synthesis;
the step of functionalization comprises:
supplying a primer support which is a polymer resin support comprising a main skeleton and $G_2$-AA- N—(CH$_2$CH$_2$—S-Trt-)$_2$ functional groups or G$_2$-AA-N—(CH$_2$CH$_2$—S-Trt-CO—NH—)$_2$ functional groups, wherein Trt represents a triphenylmethyl group or a substituted triphenylmethyl group;

the step of peptide synthesis comprises a succession of couplings of amino acids on the primer support, and wherein G$_2$ is a hydrogen atom or a protective group of amine function.

17. Method according to claim 14, in which coupling of an amino acid to the polymer resin support comprises bringing the polymer resin support into contact with an amino acid halide or with an amino acid and an activating agent selected from PyBOP, BOP, and PyBROP.

18. Method according to claim 11, wherein G$_1$ represents a protective group forming a thioether, thioester or disulphide function.

19. Method according to claim 18 wherein G$_1$ represents the triphenylmethyl group.

20. Polypeptide according to claim 9, wherein the polypeptide of formula (I) is a polypeptide of formula (XI):

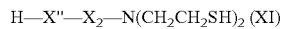
H—X″—X$_2$—N(CH$_2$CH$_2$SH)$_2$ (XI)

X$_2$ representing a peptide fragment and X″ representing an amino acid residue comprising a thiol function.

21. Polypeptide according to claim 9, wherein the polypeptide of formula (I') is a polypeptide of formula (XI'):

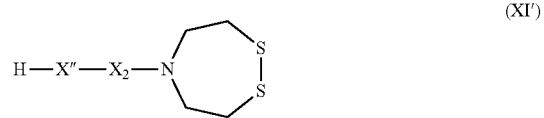

X$_2$ representing a peptide fragment and X″ representing an amino acid residue comprising a thiol function.

22. Kit for the synthesis of polypeptides comprising:
a. At least one polypeptide of formula (I) X$_1$—N(CH$_2$CH$_2$SH)$_2$ in which X$_1$ represents a peptide fragment and the group —(CH$_2$CH$_2$SH)$_2$ is bound to the C═O termination of the amino acid residue of the peptide fragment X$_1$ that is in C-terminal position, and
b. At least one polymer resin support comprising a main skeleton and NH—(CH$_2$CH$_2$—S-Trt-)$_2$ functional groups or NH—(CH$_2$CH$_2$—S-Trt-CO—NH—)$_2$ functional groups.

* * * * *

UNITED STATES PATENT AND TRADEMARK OFFICE
CERTIFICATE OF CORRECTION

PATENT NO.        : 9,029,503 B2  
APPLICATION NO.   : 13/504054  
DATED             : May 12, 2015  
INVENTOR(S)       : Melnyk et al.

Page 1 of 1

It is certified that error appears in the above-identified patent and that said Letters Patent is hereby corrected as shown below:

In the claims:

Column 45,
Lines 51 and 52, the formula should read:
--H-$X_{n-j}''$-$X_{n-j}'$- $N(CH_2CH_2SH)_2$--.

Signed and Sealed this
Twenty-sixth Day of January, 2016

Michelle K. Lee
*Director of the United States Patent and Trademark Office*